US011083907B2

United States Patent
Dapprich et al.

(10) Patent No.: US 11,083,907 B2
(45) Date of Patent: Aug. 10, 2021

(54) SUPERPARAMAGNETIC PARTICLE SCAFFOLD FOR REGENERATING DAMAGED NEURAL TISSUE

(71) Applicant: Neuropair, Inc., Princeton, NJ (US)

(72) Inventors: Johannes Dapprich, Lawrenceville, NJ (US); Karl P Dresdner, Jr., Newtown, PA (US)

(73) Assignee: NEUROPAIR, INC., Princeton, NJ (US)

( * ) Notice: Subject to any disclaimer, the term of this patent is extended or adjusted under 35 U.S.C. 154(b) by 359 days.

(21) Appl. No.: 15/731,789

(22) Filed: Aug. 1, 2017

(65) Prior Publication Data

US 2018/0064951 A1 Mar. 8, 2018

Related U.S. Application Data

(60) Provisional application No. 62/494,239, filed on Aug. 1, 2016, provisional application No. 62/371,308, filed on Aug. 5, 2016.

(51) Int. Cl.
| | | |
|---|---|---|
| *A61N 2/00* | (2006.01) | |
| *A61K 41/00* | (2020.01) | |
| *A61L 27/50* | (2006.01) | |
| *A61L 27/04* | (2006.01) | |
| *A61L 27/44* | (2006.01) | |

(Continued)

(52) U.S. Cl.
CPC ............. *A61N 2/006* (2013.01); *A61K 41/00* (2013.01); *A61L 27/04* (2013.01); *A61L 27/446* (2013.01); *A61L 27/50* (2013.01); *A61P 25/00* (2018.01); *A61L 2400/06* (2013.01); *A61L 2400/12* (2013.01); *A61L 2430/32* (2013.01);

(Continued)

(58) Field of Classification Search
CPC . A61K 41/00; A61L 2400/12; A61L 2430/32; A61N 2/006
See application file for complete search history.

(56) References Cited

U.S. PATENT DOCUMENTS

| | | |
|---|---|---|
| 6,225,109 B1 | 5/2001 | Juncosa et al. |
| 6,585,939 B1 | 7/2003 | Dapprich |

(Continued)

OTHER PUBLICATIONS

Huebner, Eric, A and Strittmatter, Stephen, M. Axon regeneration in the periferal and central nervous system. Results Probl. Cell Differ. 48:339-351, 2009.

Peiris PM, Schmidt E, Calabrese M, Karathanasis E. Assembly of linear nano-chains from iron oxide nanospheres with asymmetric surface chemistry. PLoS One. Jan. 6, 2011;6(1):e15927.

(Continued)

*Primary Examiner* — Christine H Matthews
(74) *Attorney, Agent, or Firm* — Wilson Sonsini Goodrich & Rosati

(57) ABSTRACT

The invention generally relates to a method of regenerating a nerve fiber in a damaged neural tissue of a patient, the method comprising the steps of: administering an aqueous formulation comprising superparamagnetic particles to the damaged neural tissue in the patient; applying a magnetic field in an orientation which is parallel to the nerve fiber; using the magnetic field for aligning the superparamagnetic particles; forming one or more aligned chains of the superparamagnetic particles in the magnetic field as a scaffold to guide directional growth of regenerating nerve cells; and reconnecting damaged nerve ends in the damaged neural tissue of the patient.

20 Claims, 20 Drawing Sheets

(51) Int. Cl.
  *A61P 25/00*     (2006.01)
  *H01F 1/00*      (2006.01)
  *B82Y 25/00*     (2011.01)
  *B82Y 5/00*      (2011.01)

(52) U.S. Cl.
  CPC ............... *B82Y 5/00* (2013.01); *B82Y 25/00* (2013.01); *H01F 1/0054* (2013.01)

(56) References Cited

U.S. PATENT DOCUMENTS

| | | | |
|---|---|---|---|
| 6,720,143 | B2 | 4/2004 | Juncosa et al. |
| 2006/0140871 | A1* | 6/2006 | Sillerud ............ A61K 49/1875 424/9.36 |
| 2013/0110138 | A1 | 5/2013 | Hurtado |
| 2016/0243377 | A1† | 8/2016 | Weinberg |
| 2017/0106088 | A1 | 4/2017 | Liu |

OTHER PUBLICATIONS

Lattuada, Marco, and Hatton, Alan T. (2011) Synthesis, Properties, and Applications of Janus particles. Nano Today 6:286-308.
Tian Lingling, Prabhakaran, Molamma, P., Ramakrishna, Searam. (2015) Strategies for regeneration of components of nervous system: scaffolds, cells, and biomolecules: Regenerative Biomaterials 31-45.
Antman-Passig, Merav, Shefi, Orit. (Mar. 4, 2016). Remote magnetic orientation of 3D collagen hydrogels for directed neuronal regeneration. Nano Letters, 1-18.
Bollaerts, I, Van hoecke, J, Andries, L, Groef, L, and Moons, L. (2017) Neuroinflaihmation as fuel for axonal regeneration in the injured vertebrate nervous system. Mediators of Inflammation, vol. 2017, Art. ID9478542, 14 pages.
Antman-Passig, (Mar. 4, 2016). Supporting Documents, Remote magnetic orientation of 3D collagen hydrogels for directed neuronal regeneration. Nano Letters, 1-18.

\* cited by examiner
† cited by third party

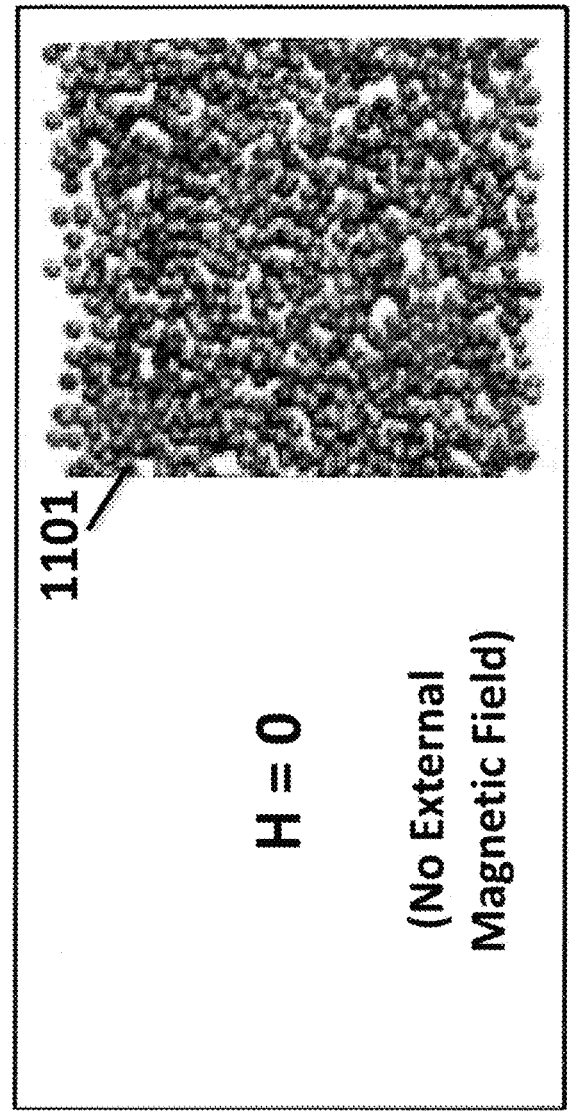 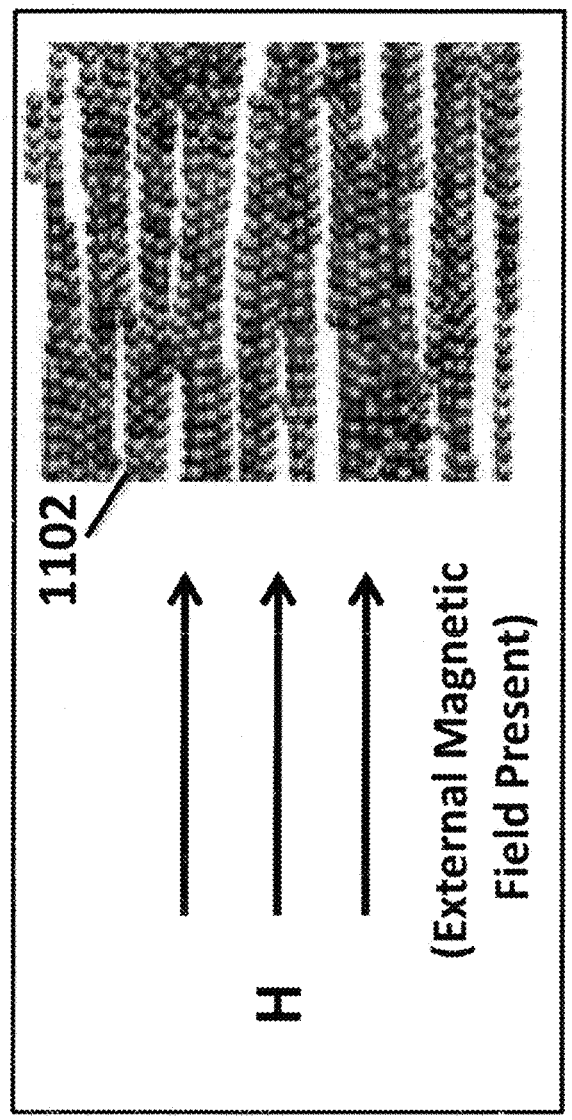
Fig. 11A
Fig. 11B

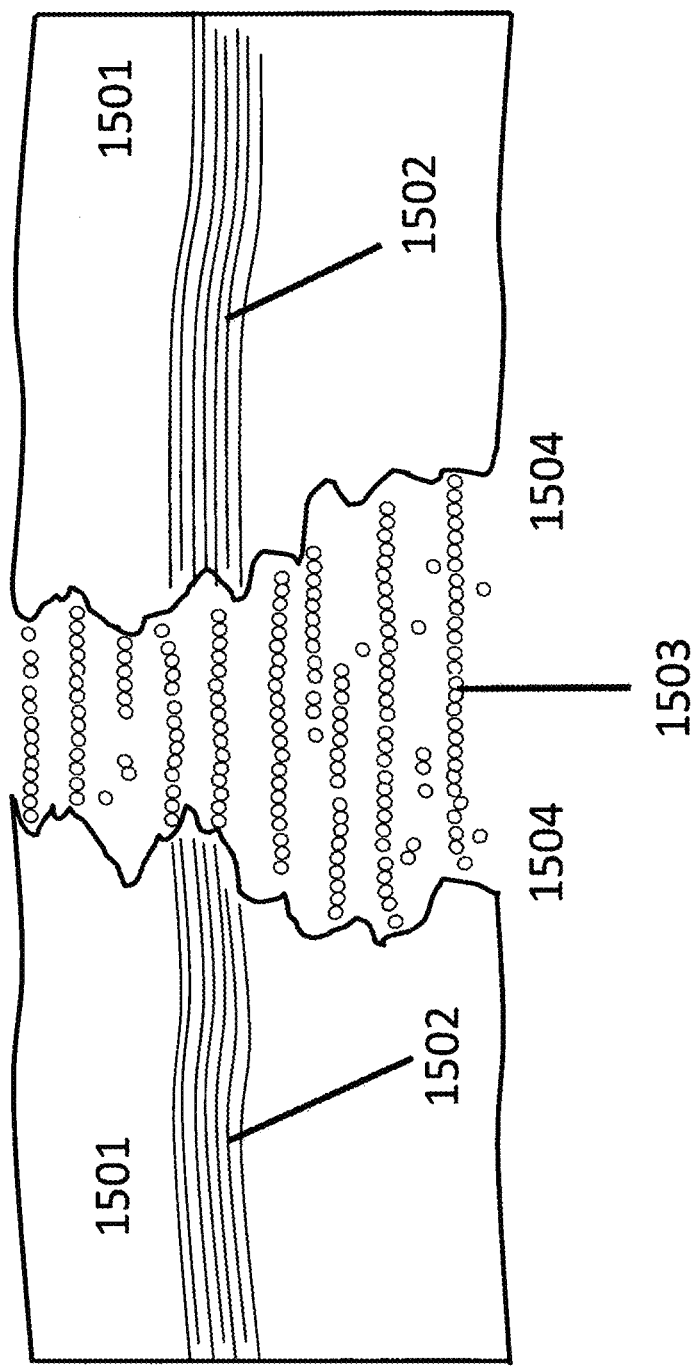

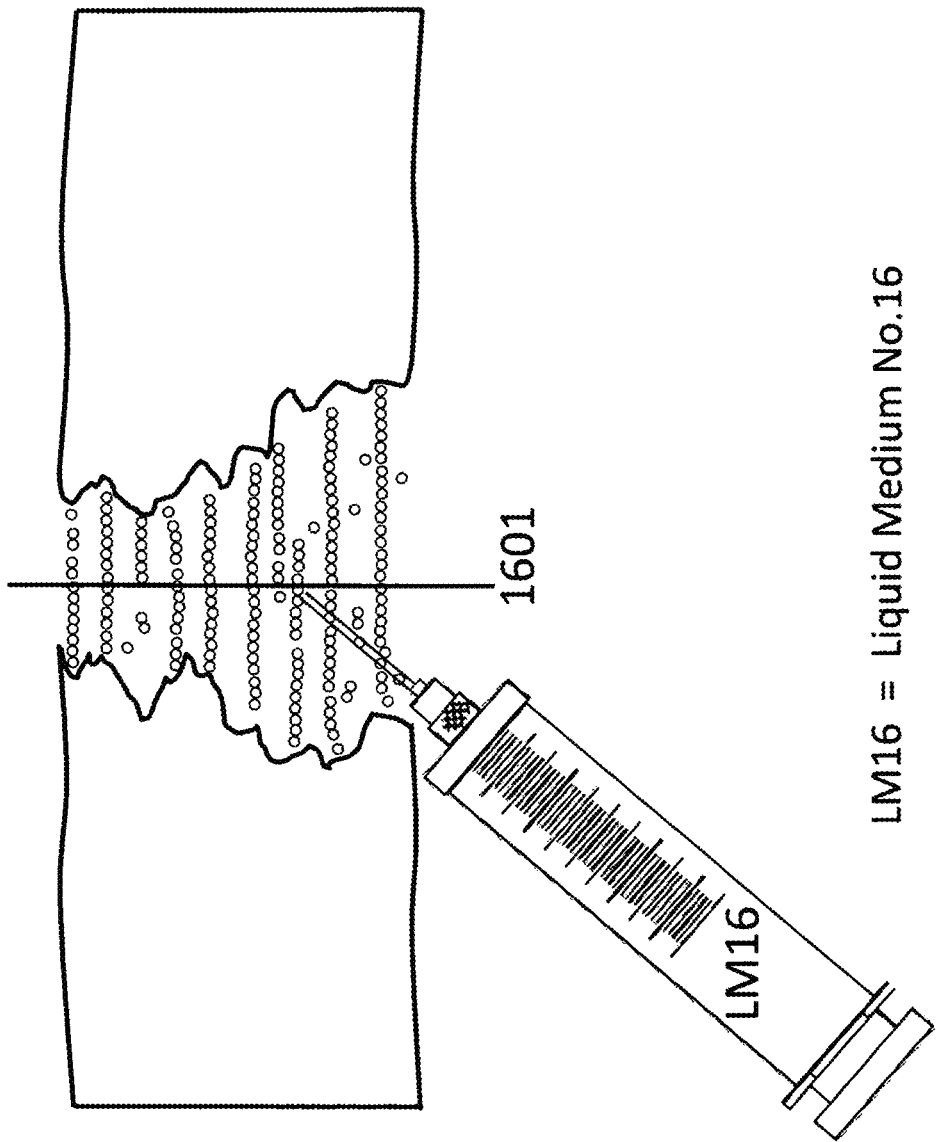

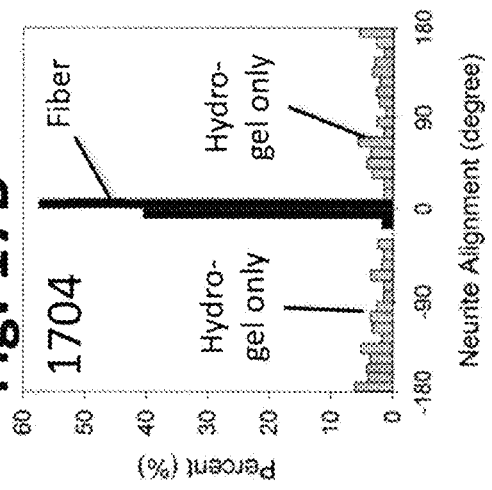
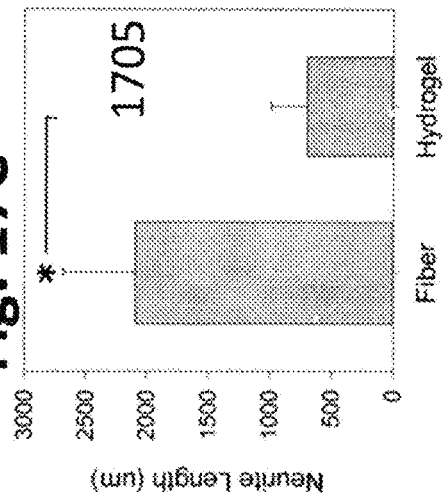
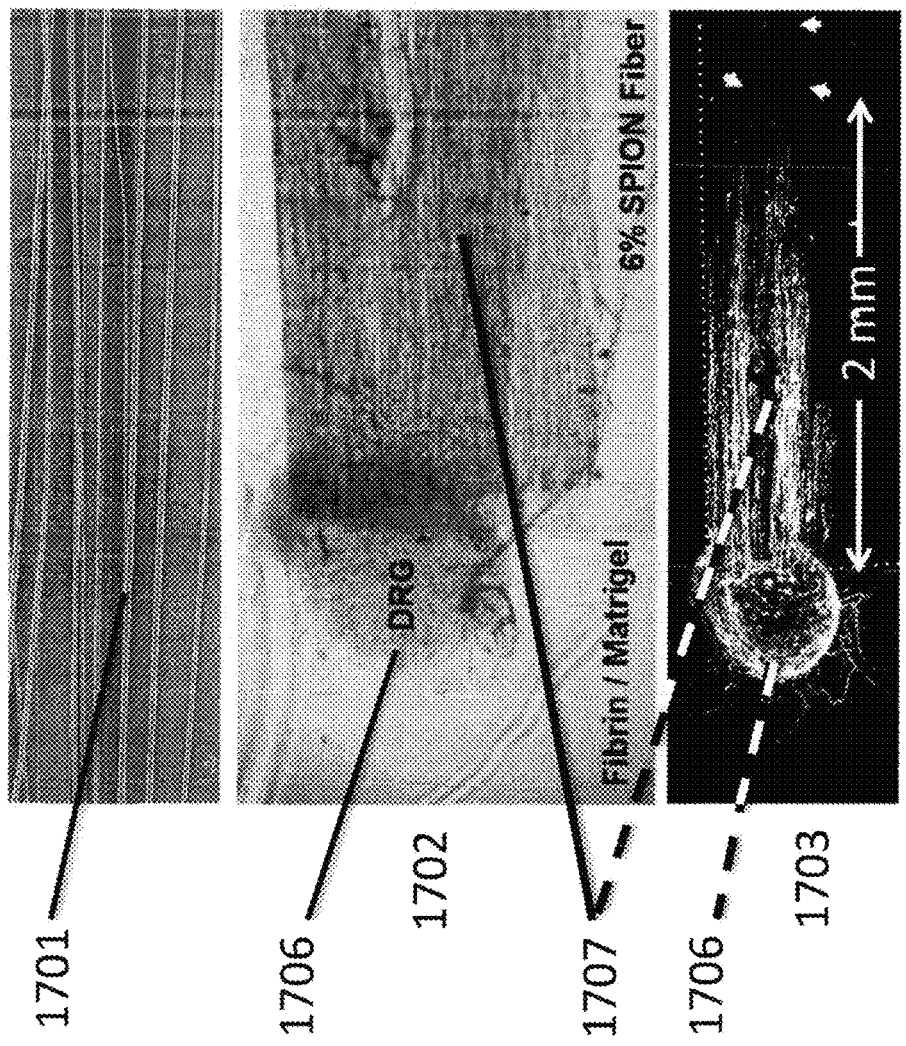

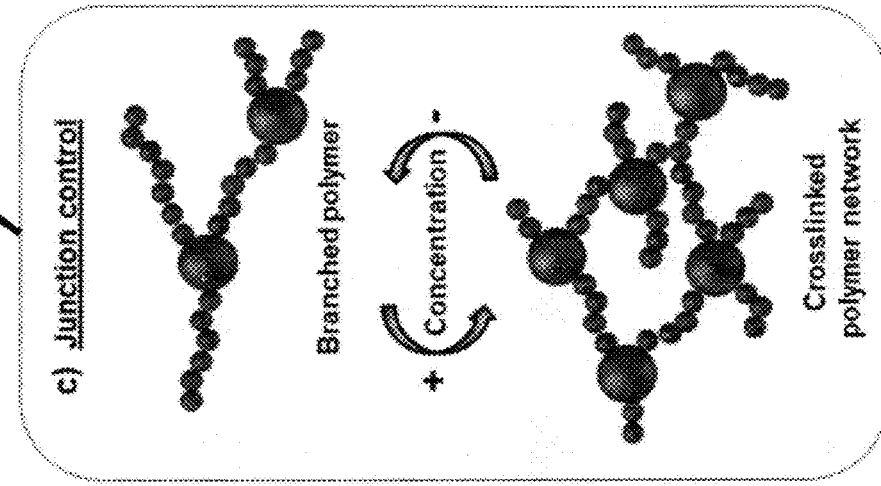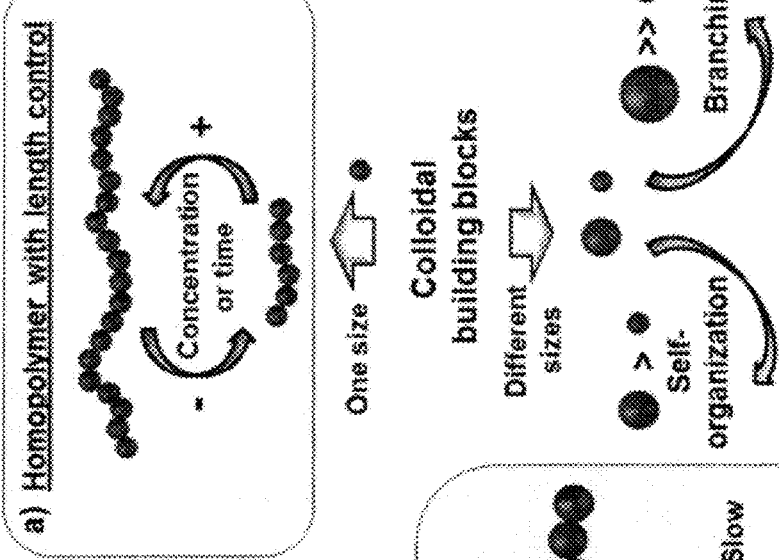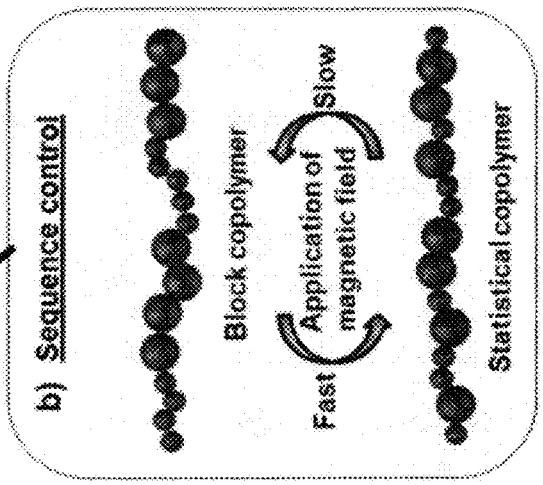

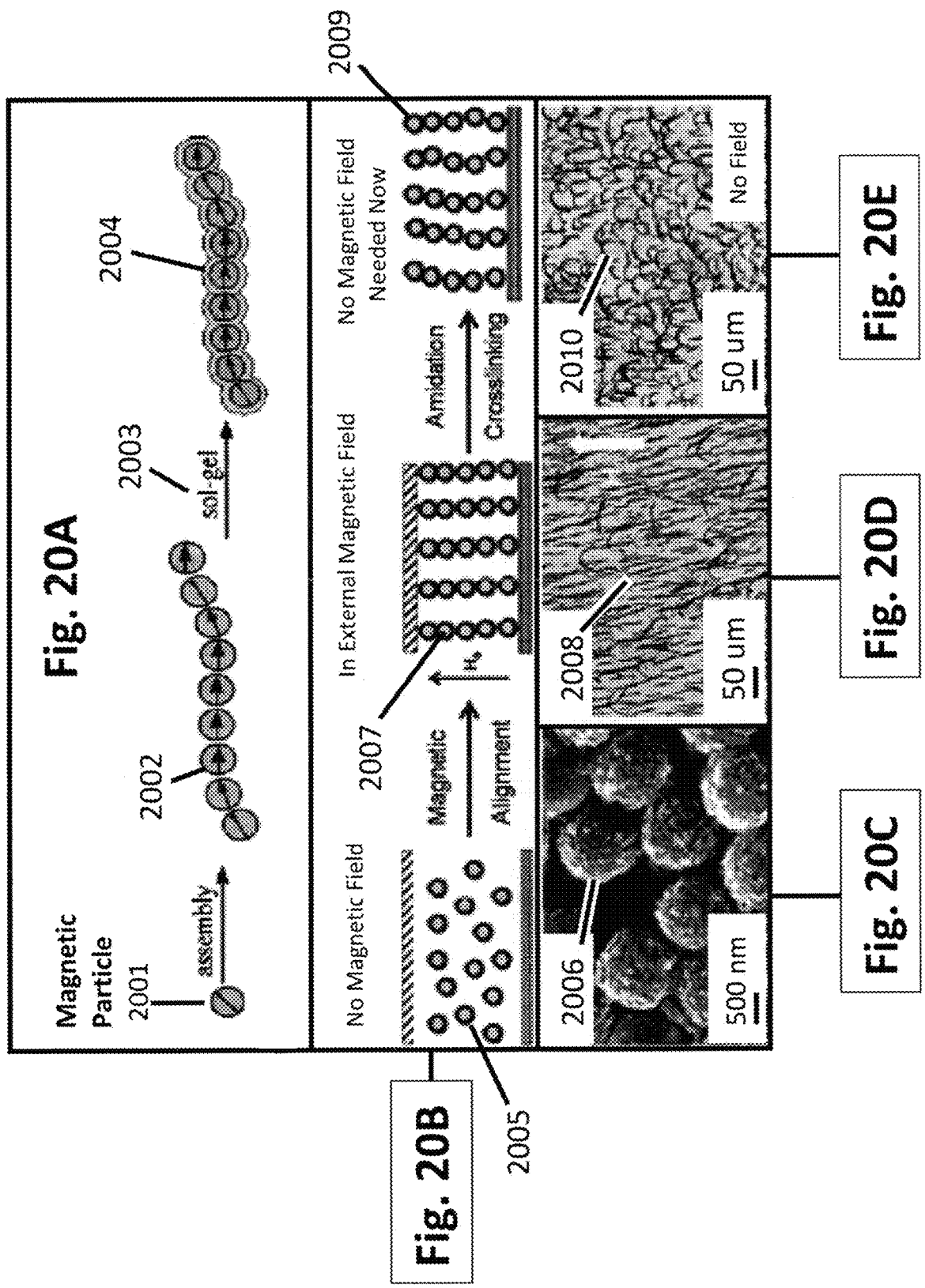

SUPERPARAMAGNETIC PARTICLE SCAFFOLD FOR REGENERATING DAMAGED NEURAL TISSUE

CROSS-REFERENCE TO RELATED APPLICATIONS

The present U.S. non-provisional patent application claims the benefit of priority of U.S. provisional patent application with Ser. No. 62/494,239 filed Aug. 1, 2016 and entitled "Method And Compositions For Creating Magnetically Aligned Scaffolds For Tissue Regeneration—Fibermag" and this U.S. provisional patent application is hereby incorporated by reference in its entirety as if fully set forth herein. In addition the present U.S. non-provisional patent application claims the benefit of priority of U.S. provisional patent application with Ser. No. 62/371,308 filed Aug. 5, 2016 and entitled "Magnetically Alignable Electrospun Poly-Lactide Fibers For Spinal Cord Injury" and this U.S. provisional patent application is hereby incorporated by reference in its entirety as if fully set forth herein.

BACKGROUND OF THE INVENTION

The invention area relates to nervous tissue damage (NTD) and CNS lesions. Every year, up to 500,000 people worldwide suffer a spinal cord injury (SCI). In the USA alone, there are 17,000 new SCI cases each year. People with a spinal cord injury are two to five times more likely to die prematurely than people without a spinal cord injury, with worse survival rates in low-income and middle-income countries. Spinal cord injury is associated with lower rates of school enrollment and economic participation, and it carries substantial individual and societal costs.

Brain injuries, cranial nerve damage, peripheral nerve damage, traumatic nervous tissue lesions and neurodegeneration drastically reduce life quality and lead to severe and often fatal impairments, largely because the central nervous system (CNS) of adult mammals retains a low capacity for regeneration into adulthood. Nervous tissue regeneration comprises the replacement of lost neurons (de novo neurogenesis) and/or the repair of damaged axons (axonal regeneration). Functional deficits persist after spinal cord injury (SCI), traumatic brain injury, stroke, and related conditions that involve axonal disconnection. This situation differs from that in the mammalian peripheral nervous system (PNS), where long-distance axon regeneration and substantial functional recovery can occur in the adult.

The invention area also relates to extracellular molecules and the intrinsic growth capacity of neurons that influence neural regenerative success. Inhibitors of regeneration include specific proteins in CNS myelin and molecules associated with the astroglial scar. The two major classes of CNS regeneration inhibitors are the myelin-associated inhibitors (MAIs) and the chondroitin sulfate proteoglycans (CSPGs). MAIs are proteins expressed by oligodendrocytes as components of CNS myelin. MAIs impair neurite outgrowth in vitro and are thought to limit axon growth in vivo after CNS damage. MAIs include Nogo-A, myelin-associated glycoprotein (MAG), oligodendrocyte myelin glycoprotein (OMgp), ephrin-B3, and Semaphorin 4D (Sema4D) (Huebner, 2009).

The astroglial scar, which forms after CNS injury, is a physical barrier to regeneration and also contains inhibitory molecules that impede axon growth. CSPGs are the main inhibitory molecules found in the glial scar and are upregulated by reactive astrocytes after CNS damage. CSPGs can be both membrane bound and secreted into the extracellular space. CSPG inhibitors include neurocan, versican, brevican, phosphacan, aggrecan, and NG2 (Huebner, 2009). Other CNS axon regeneration inhibitors (ARIs) that are not present in myelin or the glial scar include repulsive guidance molecule (RGM) and semaphorin 3A.

The invention area also relates to neuronal and glial cell cAMP levels. Increasing cAMP levels by intra-ganglionic injection of a membrane-permeable cAMP analog, dibutyrylcAMP (db-cAMP), mimics the growth-promoting effects of a conditioning lesion, promoting regeneration of sensory axons within the spinal cord. Rolipram, a phosphodiesterase 4 inhibitor, increases cAMP by interfering with its hydrolysis. The cAMP elevation activates protein kinase A (PKA) and induces CREB-mediated transcription of various growth-associated genes, including IL-6 and arginase I. Subsequent synthesis of polyamines by arginase I has been proposed as a possible mechanism by which cAMP increases neurite growth (Huebner, 2009).

In addition, the invention area relates to NTD debris clearance in the CNS which may impede axonal re-growth. The cell-autonomous failure of axotomized CNS neurons to induce growth-promoting genes also limits brain and spinal cord repair (Huebner, 2009).

The invention area also relates to the preservation of injured cells followed by axonal regeneration. There is death of the damaged cells at the epicenter of the lesion, including neurons, oligodendrocytes, and astrocytes. After the primary insult, secondary processes, such as excitotoxicity and oxidative stress may cause additional loss of neurons and supporting cells. Furthermore, interrupted descending and ascending axonal tracts have debilitating consequences, and although proximal segments typically survive, they do not regenerate spontaneously. Restoration of motor and sensory tracts via axonal regeneration is believed to be the most promising way to reverse paralysis after spinal cord injury.

The invention area also relates to the problem of an acute inflammatory response taking place rapidly after traumatic CNS lesions, which affects neuronal regeneration in a nervous tissue damage area. Microglial cells are one mediator of CNS inflammation and, are among the first cells to respond to damage. Microglial cells become activated, amoeboid, proliferate, migrate to the injury site, and start to produce a variety of pro-inflammatory cytokines and anti-inflammatory cytokines. Cytokine recruit neutrophils and macrophages to the damaged nervous tissue. Also, astrocytes, microglia, and macrophages begin to form a regeneration-inhibiting glial scar.

The acute inflammatory response may increase CNS damage and associated pathology. In support of this view is the observation that after spinal cord injury, depletion of peripheral macrophages and administration of an anti-inflammatory drug enhances axonal regeneration and improves functional recovery. However, more recent evidence suggests that the inflammatory response can also positively contribute to regeneration. There are also conflicting results regarding the negative or positive effect of acute inflammation in CNS regeneration (Bollarets, 2017). Further investigation of its mediator cells and their key regulatory switches is needed to understand how successful regeneration can be implemented. Another variable is the fact that aging processes affect regeneration and the innate immune system.

The invention area also relates to the observation that axonal pathways typically represent a unidirectional and aligned architecture allowing systematic axonal development within the tissue. Following a traumatic injury, the intricate architecture suffers disruption, leading to inhibition of growth and loss of guidance. Due to the limited capacity of the human body to regenerate axonal pathways on its own, it is highly desirable to have biomimetic approaches that have the capacity to graft a bridge across the lesion by providing optimal mechanical and biochemical cues for tissue regeneration. And for central nervous system injury, one more extra precondition is compulsory: creating a surrounding for neural regeneration that is less inhibitory for the desirable, nerve-regenerating cells (Tian, 2015).

Furthermore, the invention area relates to the role of neural stem cells (NSCs). NSCs and olfactory ensheathing glial cells (OEGs) have important roles in the nervous system. NSCs are able to self-renew and generate main neuronal and glial cells. Human NSCs are able to differentiate into neurons, astrocytes and oligodendrocytes, and achieve full neuronal maturation but are affected by their external environment's growth factors, dynamic forces, and possibly other cell types. Transplantation of NSCs into the adult CNS may help functional recovery, remodel the NTD and increase the tissue plasticity. CNS OEGs keep proliferating throughout the life, and support and guiding growth of newly formed axons. Thus CNS OEGs may be important aids for CNS neural repair. Notably, a CNS glial scar cannot block OEG migration and OEGs are able to enter both gray and white matter, and once there possibly attract regenerating axon (Tian, 2015)

The invention area also relates to the development of supportive tissues and scaffolds to promote neuronal regeneration (Antman-Passig, 2017). Guiding and directing neuronal outgrowth during the regeneration period may enhance neuronal repair and recovery. Methods which have been used to fabricate scaffolds with aligned fibrils as neuronal cell-directing cues for assisting neuronal regeneration include electro-spinning, microfluidics, forcing an alignment of collage fibers using magnetic nanoparticles in a magnetic field, strain-induced alignment, and prefabrication of prescribed patterns within the 3D constructs. Another approach being explored is using magnetic particle embedded electrospun polylactic acid fibers or another magnetic particle embedded polymer that can be injected into the spinal cord injury site, then aligned in situ using an external magnetic field.

Furthermore, the invention area is related to solving the practical clinical limitations of directing spinal cord regeneration. Firstly, spinal cord lesions are often diagnosed and clearly visible by magnetic resonance imaging (MRI), yet very difficult and risky to access surgically. Minimally invasive techniques that provide equivalent or improved treatment results are therefore clearly desirable compared to traditional, open surgery. Secondly, the implantation of a prefabricated/3D-printed or a custom-manufactured oriented fiber plug that is customized to the patient's particular lesion is a complex, time-consuming and expensive process. The implantation of a (currently hypothetical) prefabricated/3D-printed or a custom-manufactured oriented, functional fiber plug that is customized to the patient's particular lesion would also need: (a) an assessment and accurate three-dimensional shape determination of the void that is to be filled in the lesion cavity; (b) the transfer of that information to a 3D-modeling software; (c) the de-novo fabrication and/or the modification of pre-fabricated fiber plugs that should precisely match the shape of the void; and (d) the successful surgical insertion, adjustment and adoption by the human body of this customized fiber plug. The overall process would require considerable amounts of time, skill and resources and pose considerable risk, discomfort and cost for the patient. These resources may not be readily available during the time window in which reconstructive intervention of spinal cord injury is best attempted, which is believed to be prior to NTD scar tissue formation by glial cells. Also, the implantation of a prefabricated/3D-printed or a custom-manufactured oriented fiber plug that is customized to the patient's particular lesion would need a highly specialized expertise and expensive equipment.

BRIEF SUMMARY OF THE INVENTION

The invention generally relates to a method of regenerating a nerve fiber in a damaged neural tissue of a patient, the method comprising the steps of: administering an aqueous formulation comprising superparamagnetic particles to the damaged neural tissue in the patient; applying a magnetic field in an orientation which is parallel to the nerve fiber;—using the magnetic field for aligning the superparamagnetic particles; forming one or more aligned chains of the superparamagnetic particles in the magnetic field as a scaffold to guide directional growth of regenerating nerve cells; and reconnecting damaged nerve ends in the damaged neural tissue of the patient.

In some preferred embodiments, the general invention method further comprises an earlier step of functionalizing surfaces of the superparamagnetic particles with one or the more chemical moieties prior to administering the aqueous formulation comprising the superparamagnetic particles to the damaged neural tissue in the patient, wherein the surfaces of the superparamagnetic particles are functionalized with the one or more chemical moieties selected from the group consisting of a carbohydrate, a protein, a lipid, a glass, an oligosaccharide, a peptides, a cross-linking agent, a thiol, a sulfide, an oxide, a sulfhydryl, a sulfide, a disulfide, a sulfinyl, a sulfoxide, a sulfonyl, a sulfone, a sulfinic acid, a sulfino, a sulfonic acid, a sulfo, a thioketone, a carbonothioyl, a thial, a primary amine, a secondary amine, a tertiary amine, a carboxylate, a carboxyl, an alkoxy, a hydroperoxy, a peroxy, an alkyl, an alkene, an alkyne, an aryl derivative, a halo group, a hydroxyl, a carbonyl, an aldehyde, an acyl halide, an ester, a carbonate ester, an ether, a hemi-acetal, a hemiketal, a ketal, an orthoester, a methyledioxy, a cycloalkyl, a heterocyclic, a heteroaryl, an orthocarbonate ester, a carboxamide, a primary ketimine, a secondary ketamine, a primary aldimine, a secondary aldimine, an imide, a nitro, a phosphonic acid, a phosphate, a phosphodiester, a nitrile, an isonitrile, an isocyanate, a an antibody, a pharmaceutical excipient, a pH buffer, a cerium oxide nanoparticle, a manganese dioxide nanoparticle, EDTA, EGTA, NTA, HEDTA, a cytokine, and a combination thereof.

In other preferred embodiments, the general invention method further comprises an earlier step of functionalizing the surfaces of the superparamagnetic particles with the one or more chemical moieties is for promoting a chemical bonding between the superparamagnetic particles when the magnetic field is aligning the superparamagnetic particles and forming the one or more aligned chains of the superparamagnetic particles parallel to the nerve fiber.

Some embodiments of the invention are methods wherein the earlier step of functionalizing the surfaces of the superparamagnetic particles with the one or more chemical moieties is for forming Janus superparamagnetic particles.

The invention embodiments include methods wherein the functionalized Janus superparamagnetic particles have a Side A functionalized with a first chemical moiety and have a Side B functionalized with a second chemical moiety.

The invention embodiments include methods wherein the earlier step of functionalizing the surfaces of the superparamagnetic particles with the one or more chemical moieties for forming the Janus superparamagnetic particles is conducted in the presence of a magnetic field.

The invention embodiments include methods wherein the functionalized Janus superparamagnetic particles have the Side A surface functionalized with the first chemical moiety as a thiol and have the Side B surface functionalized with the second chemical moiety as a primary amine. Other invention embodiments include methods wherein the functionalized Janus superparamagnetic particles have the Side A surface functionalized with the first chemical moiety as a thiol and have the Side B surface functionalized with the second chemical moiety as a primary amine.

The functionalized Janus superparamagnetic particles can have the Side A functionalized with the first chemical moiety as the carboxylic acid and can have the Side B functionalized with the second chemical moiety as the primary amine.

The functionalized Janus superparamagnetic particles can have the Side A functionalized with the first chemical moiety as the carboxylic acid and can have the Side B functionalized with the second chemical moiety as the primary amine.

In some invention method embodiments, the aqueous formulation comprising the superparamagnetic particles further comprises a molecule selected from the group consisting of a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4-sulfation on astrocyte-derived chondroitin sulfate proteoglycan, an inhibitor of chondroitin sulfate proteoglycan phosphacan, an inhibitor of chondroitin sulfate proteoglycan neurocan, a chondroitinase-ABC, an inhibitor of chondroitin sulfate proteoglycan 4, an inhibitor of neuron-glial antigen 2, an antibody to chondroitin sulfate proteoglycan 4, an antibody against neuron-glial antigen 2, an inhibitor of glial cell expression of chondroitin sulfate proteoglycan 4, an inhibitor of glial cell expression of neuron-glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI-35, an antibody against myelination inhibitory factor NOGO, an anti-oxidants, cerium oxide nanoparticles, an amino acid, a phospholipid, a lipid, a vitamin, an anticoagulant, and a combination thereof.

In some invention method embodiments, the aqueous formulation comprising the superparamagnetic particles further optionally comprises a carrier which is microspheres, porous particles, a gel, a hydrogel, a multiphase solution, a colloid, a capsule, a microcapsule, a liposome, an isotonic saline, a cerebrospinal fluid, or a combination thereof.

In other preferred embodiments, the general invention method further comprises the step of stabilizing the aligned chains of the superparamagnetic particles in the magnetic field using a cross-linking polymer architecture for locking the aligned chains of the superparamagnetic particles into place after the step in claim 1 of using the magnetic field for aligning the superparamagnetic particles and forming the one or more aligned chains of the superparamagnetic particles in the magnetic field as the scaffold to guide directional growth of regenerating nerve cells.

In other preferred embodiments, the general invention method further comprises the step of stabilizing the aligned chains of the superparamagnetic particles in the magnetic field using a cross-linking polymer architecture for locking the aligned chains of the superparamagnetic particles into place after the step of using the magnetic field for aligning the superparamagnetic particles in the orientation which is parallel to the nerve fiber orientation in the damaged neural tissue and forming the one or more aligned chains of the superparamagnetic particles in the magnetic field in the orientation which is parallel to the nerve fiber orientation in the damaged neural tissue, and before the step of using the one or more aligned chains of the superparamagnetic particles in the orientation which is parallel to the nerve fiber orientation in the damaged neural tissue as a scaffold for regenerating the nerve fiber in the damaged neural tissue of the patient. In some invention method embodiments, the aligned chains of the superparamagnetic particles that are the scaffold for regenerating the nerve fiber in the damaged neural tissue of the patient are stabilized by a cross-linking polymer architecture.

In some invention method embodiments, the cross-linking polymer architecture for stabilizing the aligned chains of the superparamagnetic particles is selected from the group consisting of a cross-linking homopolymer of the surface functionalized superparamagnetic particles, a cross-linking copolymer of different surface functionalized superparamagnetic particles, a cross-linking junction controlled branched polymer of the surface functionalized superparamagnetic particles, and a combination thereof.

In some invention method embodiments, the cross-linking polymer architecture for stabilizing the aligned chains of the superparamagnetic particles is formed using molecules selected from the group consisting of psoralen, methyl methacrylate, avidin, streptavidin, antibodies, antigens, ligands, biotin, laminin, fluorescein, DNA hybridization molecules, DNA origami, DNA dendrimers, aptamers, protein-protein binding, protein-DNA binding, metal ion chelators, His-tags, polyethylene glycol-linkers, agarose, acrylamide, collagen, phase transfer catalysts, and any combination thereof.

Some invention method embodiments further comprise the step of removing the magnetic field which is parallel to the nerve fiber orientation after the step of stabilizing the aligned chains of the superparamagnetic particles using the cross-linking polymer architecture.

In some invention method embodiments, the superparamagnetic particles have dimensions selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination thereof.

In some invention method embodiments, the magnetic field has a strength between about 5 milli Tesla to about 500 milli Tesla.

In some invention method embodiments, the damaged neural tissue of the patient is in the spinal cord of the patient. In some invention method embodiments, the damaged neural tissue of the patient is in the peripheral nervous system of the patient. In some invention method embodiments, the damaged neural tissue of the patient is in the optic nerve of the patient.

In some invention method embodiments, the cross-linking polymer architecture for stabilizing the aligned chains of the superparamagnetic particles is formed using molecules selected from the group consisting of avidin, streptavidin, biotin, laminin, DNA hybridization molecules, and any combination thereof.

In some invention method embodiments, the general invention method further comprises an earlier step of implanting the neural tissue from the patient into an area of the damaged neural tissue of the patient prior to the step of administering the aqueous formulation comprising the superparamagnetic particles to the damaged neural tissue area in the patient.

In some preferred invention method embodiments, the superparamagnetic particles have a dimension of between about 0.5 microns to about 20 microns in diameter.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 further depicts Step 1 of a process for chemical group functionalization of a magnetic field sensitive Janus particle. In Step 1, the liquid medium 1 is preferably water at pH 7.2-8.5, and the DTSSP is 3,3'-dithiobis(sulfo-succinimidyl propionate) which is a water soluble thiol reagent. An amide bond forms between a thiol reagent DTSSP and a primary amine of a flat surface 101. This amidation immobilizes the DTSSP to flat surface 101. The immobilized amidated thiol reagent is then used in Step 2.

FIG. 2 further depicts Step 2 of a process for chemical group functionalization of a magnetic field sensitive Janus particle. In Step 2, a uniform magnetic field H is imposed perpendicular to the surface 201 on which is the immobilized amidated thiol reagent DTSSP from Step 1 in LM1.

Superparamagnetic particles 202 are not perfectly round but in the imposed uniform H magnetic field perpendicular to surface 201 advantageously develop a magnetic moment parallel in alignment to the imposed uniform magnetic H field regardless of their imperfection in roundness. The primary amine functionalized superparamagnetic particle 202 magnetic moment is depicted by the arrow on the particle. The mixture of step 2 in the magnetic field H is then used in Step 3.

Figure 3:
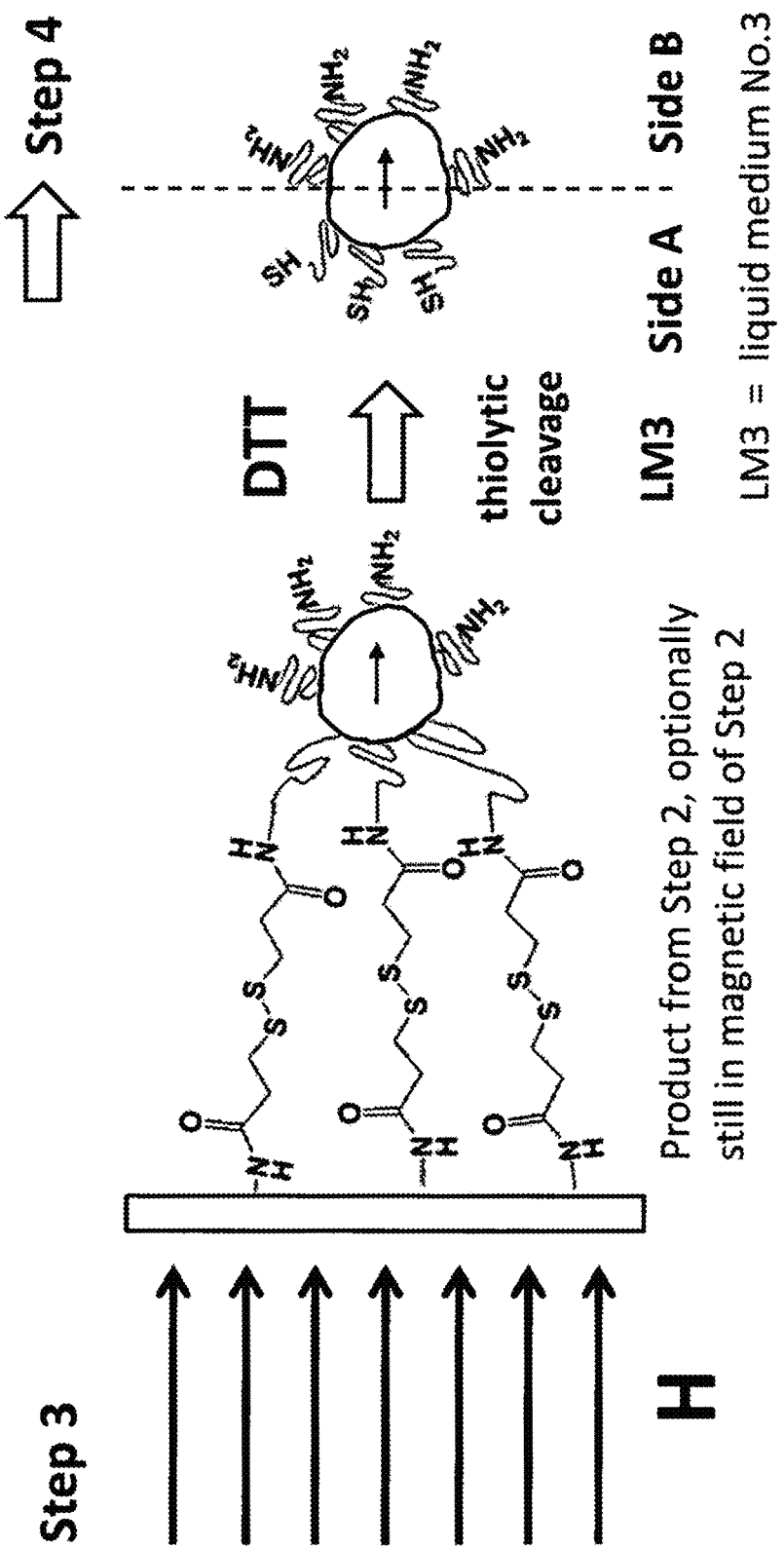

FIG. 3 depicts Step 3, the thiolytic cleavage of magetically oriented Janus particles from a surface, of a process for chemical group functionalization during the manufacture of a magnetic field sensitive Janus particle. FIG. 3 further depicts Step 3 of a process for chemical group functional- ization of a magnetic field sensitive Janus particle. In Step 3, a uniform magnetic field H is imposed perpendicular to the surface 201 on which is the immobilized amidated thiol reagent DTSSP in LM1. While in the uniform magnetic field H, the primary amine functionalized superparamagnetic particle 202 from Step 1 in LM2 reacts with the carbonyl carbon of the sulfo-succinimidyl propionate of the immobilized thiol reagent to form an amide which is held on the flat surface 201. Then addition of dithiotheitol (DTT) in liquid medium 3 (LM3) which is pH 7.0-8.0 water causes thiolytic cleavage of the disulfide bond in the immobilized amidated thiol reagent DTSSP to surface 201. The primary amine functionalized superparamagnetic particle now is a Janus particle with a Side A which has thiol (—SH) group functionalization, and with a Side B which has a primary amine functionalization. After cleavage, each particle's intrinsic magnetic moment remains aligned with functionalized Side A and Side B when an external magnetic field is present. The now formed Janus (thiol Side A-amine Side B) functionalized superparamagnetic particle is in aqueous liquid medium 3 (water at pH 7-8). Optionally, the Janus functionalized superparamagnetic particle remains in the uniform magnetic field, but in any event is then next used in Step 4.

The Janus functionalized superparamagnetic particles can be frozen, lyophilized or freeze-dried to minimize Janus particle chemistry that depends on an aqueous liquid medium or room temperature to clump the particles. Other molecules can be added to slow Janus functionalized superparamagnetic particle collisions such as a salt or a sugar, or a polyethylene glycol, The FIG. 3 Step 3 process is readily scaled up using a microfluidics device. See for example, Dapprich U.S. Pat. No. 6,585,939 and Juncosa U.S. Pat. Nos. 6,225,109 and 6,720,143 on microfluidic device designed and utilities. Note that the size of the magnetic particles used in Peiris (2011) are large (100 micron diameter) relative to CNS axons which are 0.75 to about 20 microns in diameter. Therefore, we prefer to buy and use primary amine functionalized superparamagnetic particle which are 0.5 to 10 microns diameter to follow the protocol by Peiris (2011) but carry it out on a flat surface, such as in a microfluidic reaction chamber that repeatedly gets flushed and refilled to enable higher throughput production of the particles. This scale up is not a primary concern in this example for making the Janus (thiol Side A-amine Side B) functionalized superparamagnetic particle. However, note that for us the surface 201 is preferably flat, or oriented to be perpendicular to the external magnetic field. In contrast, in the Peiris (2011) protocol, the surface 201 is a column of large particles on which the synthesis is carried out (with the surface functional groups oriented in any direction.

Figure 4:
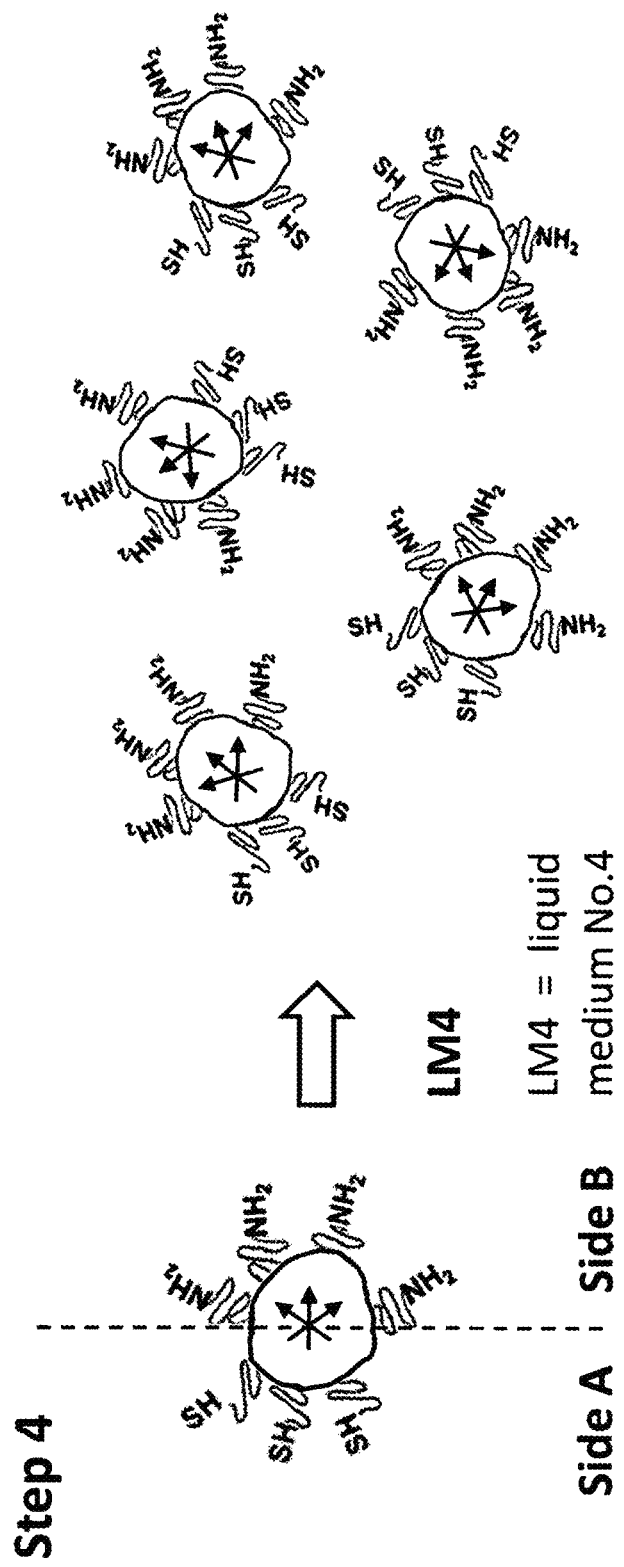

FIG. 4 depicts Janus (thiol Side A amine Side B) functionalized superparamagnetic particles in a stabilizing liquid medium 4 (LM4) in the absence of an external magnetic field. The particles are able diffuse and rotate in LM4 and their internal magnetic moment can fluctuate. FIG. 4 further depicts Janus (thiol Side A-amine Side B) functionalized superparamagnetic particle in a stabilizing liquid medium 4 (LM4). Preferably the superparamagnetic Janus functionalized particles have an average diameter in an aqueous isotonic saline medium (AISM) selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination of diameters thereof. Examples of stabilizing liquid medium 4 (LM4) are: pH 7-8 buffered water with dithiothreitol (DTT) or a faster acting disulfide reducing agent such as (N,N'dimethyl-N,N'-bis (mercapto-acetyl) hydrazine (DMH), bis(2-mercaptoethyl) sulfone (BMS), meso-2,5-dimercapto-N,N,N',N'-tetramethyladipamide (DTA).

Figure 5:
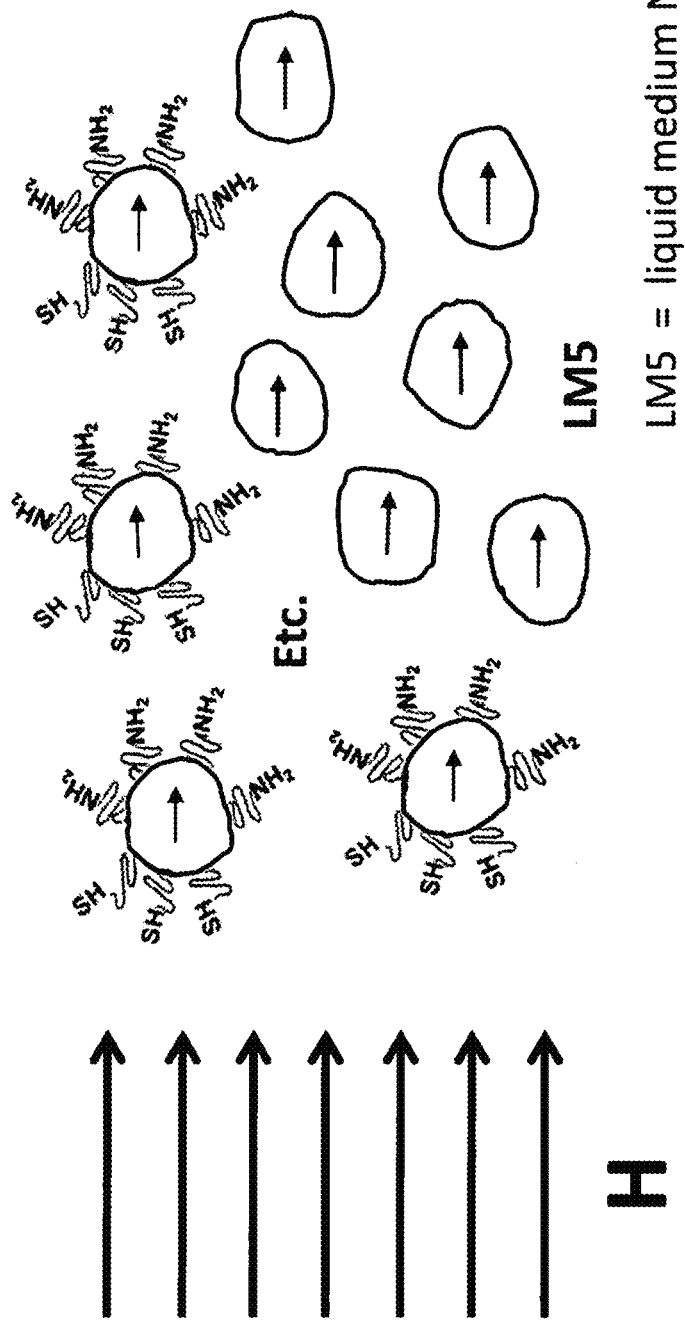

FIG. 5 depicts Janus (thiol Side A-amine Side B) functionalized superparamagnetic particles in a stabilizing liquid medium 5 (LM5) in the presence of an externally applied magnetic field as used during treatment. The particles and their internal magnetic moments are confined in their rotation and align with the externally applied magnetic field.

Figure 6:
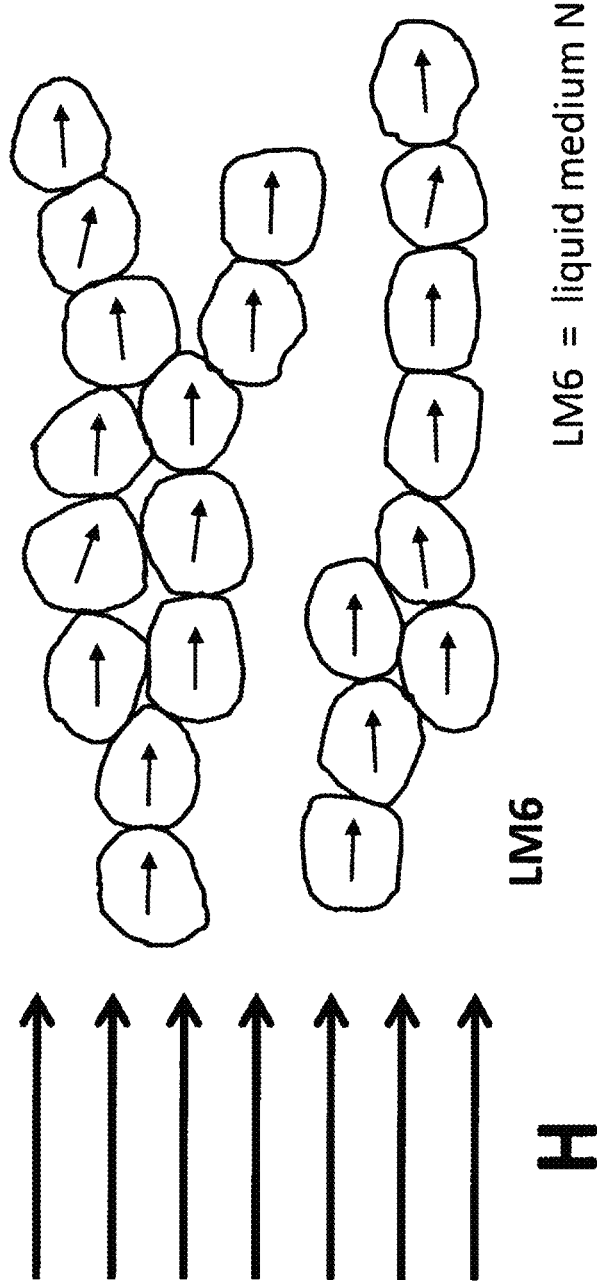

FIG. 6 depicts proximity-based, non-directional cross-linking of functionalized superparamagnetic particles in a stabilizing liquid medium 6 (LM6), forming linear and crosslinked structures in the presence of an externally applied magnetic field. FIG. 6 further depicts a preferential orientation of individual particle magnetic moments with respect to the particle shape in the presence of an externally applied magnetic field. There is recurring and consistent orientation in a field resulting in physical reorientation which is a rotation with Brownian relaxation of the individual particles and/or of their internal magnetic moment (Neel relaxation), and an alignment of the particles and their magnetic moment with the external magnetic field.

One embodiment of the present invention is a method of treating a person suffering neural tissue damage at a location in their body. The method of treatment comprises the steps of: (1) administering an aqueous formulation of superparamagnetic particles to the location of the body suffering neural tissue damage with the neural tissue damage; (2) imposing a magnetic field in a direction parallel to the direction needing a regeneration of the neural tissue at the site of the neural tissue damage; and (3) using a superparamagnetic particle scaffold at the site of the neural tissue damage for regenerating damaged neural tissue.

The superparamagnetic particles can be administered by a syringe to a damaged neural tissue area. In the damaged neural tissue area, the administered superparamagnetic particles are treated to a magnetic field. The magnetic field aligns the superparamagnetic particles and magnetizes them to become attracted to each other. Thus in the magnetic field, the superparamagnetic particles form into a multiple number of parallel series of linear particles. This parallel network of aligned particles forms a scaffold of these particles for regenerating damaged neural tissue and the formulation is deliverably situated in the nervous tissue lesion.

Figure 7:
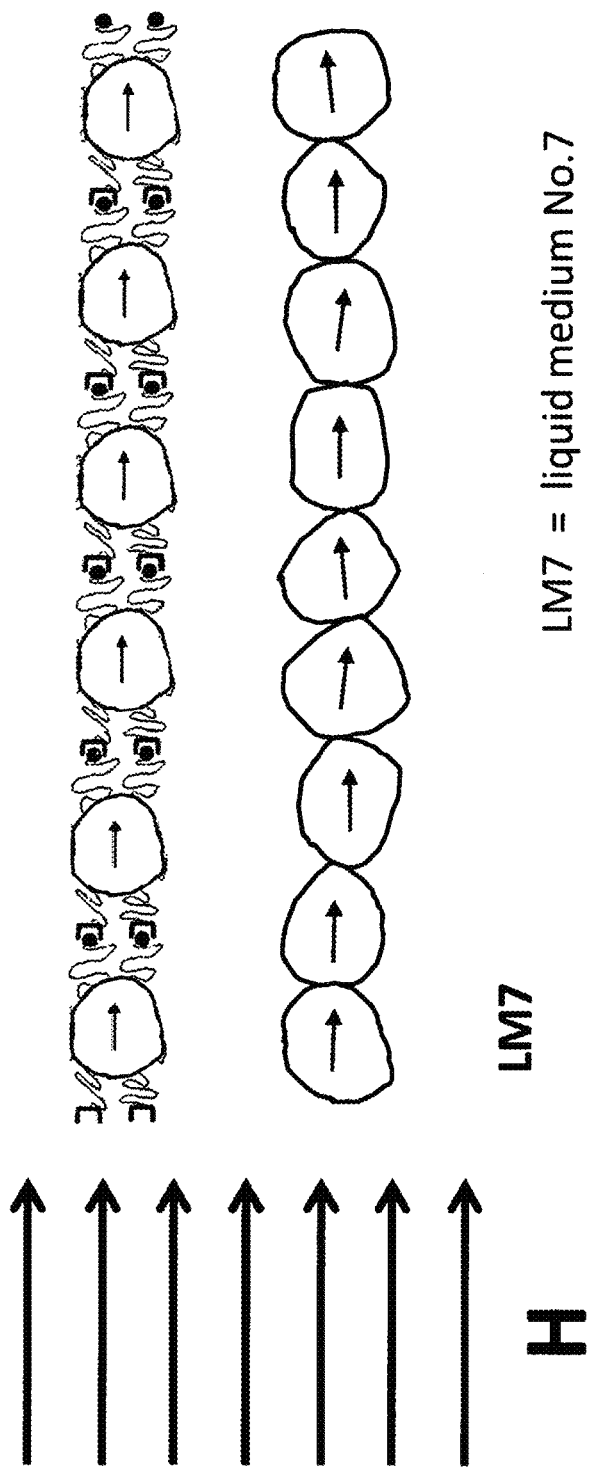

FIG. 7 depicts Janus (Side A-Side B) functionalized superparamagnetic particles in a stabilizing liquid medium 7 (LM7) forming improved, linear, Janus-type cross-linked, single-stranded chains and structures in the presence of an externally applied magnetic field. FIG. 7 further depicts a result of Step 7 which is an introduction of magnetic field in the patient at nervous tissue lesion. The magnetic field causes the particles and their magnetic moment with the external magnetic field which then causes the particles magnetic moment alignment and particle chains formation. The particles can undergo proximity-based cross-linking which can be controlled by additives, such as hydrogels which can be added to slow or reduce the extent of cross-linking. Optionally, the particles can bind and crosslink at all surfaces, which creates more chances of parallel and branched connections.

FIGS. 8A and 8B depict magnetic resonance (MRI) images of a contusive spinal cord injury. Arrows 801, 802, 803 points to areas of the injury. A): T1W (T1-weighted image); B): T2W (T2-weighted image).

Figure 9:
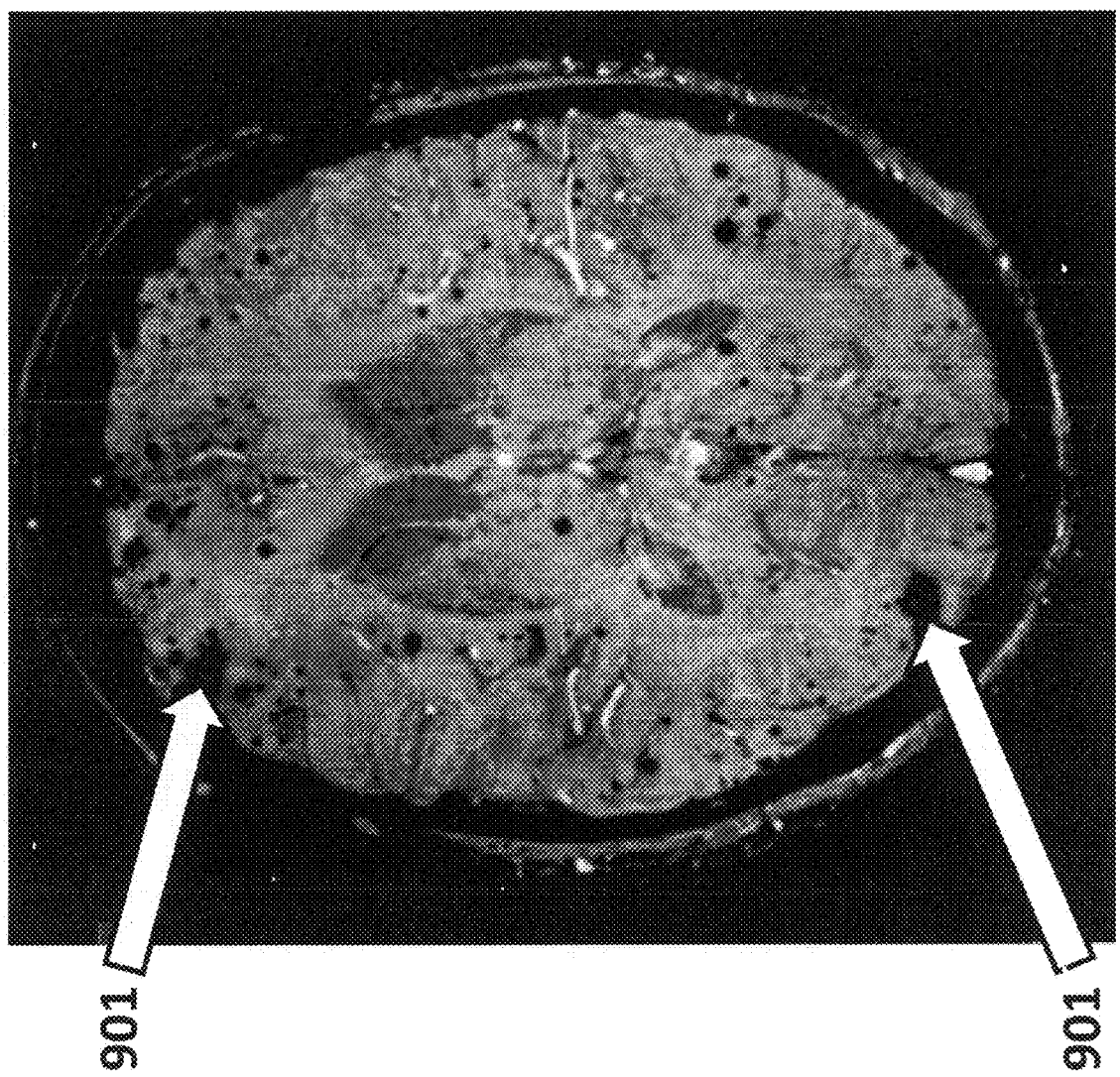

FIG. 9 depicts a magnetic resonance (MRI) brain scan of an individual with traumatic brain injury. The holes (black) depict regions of damage. Large injury sites are depicted using white arrows 901.

Figure 10:
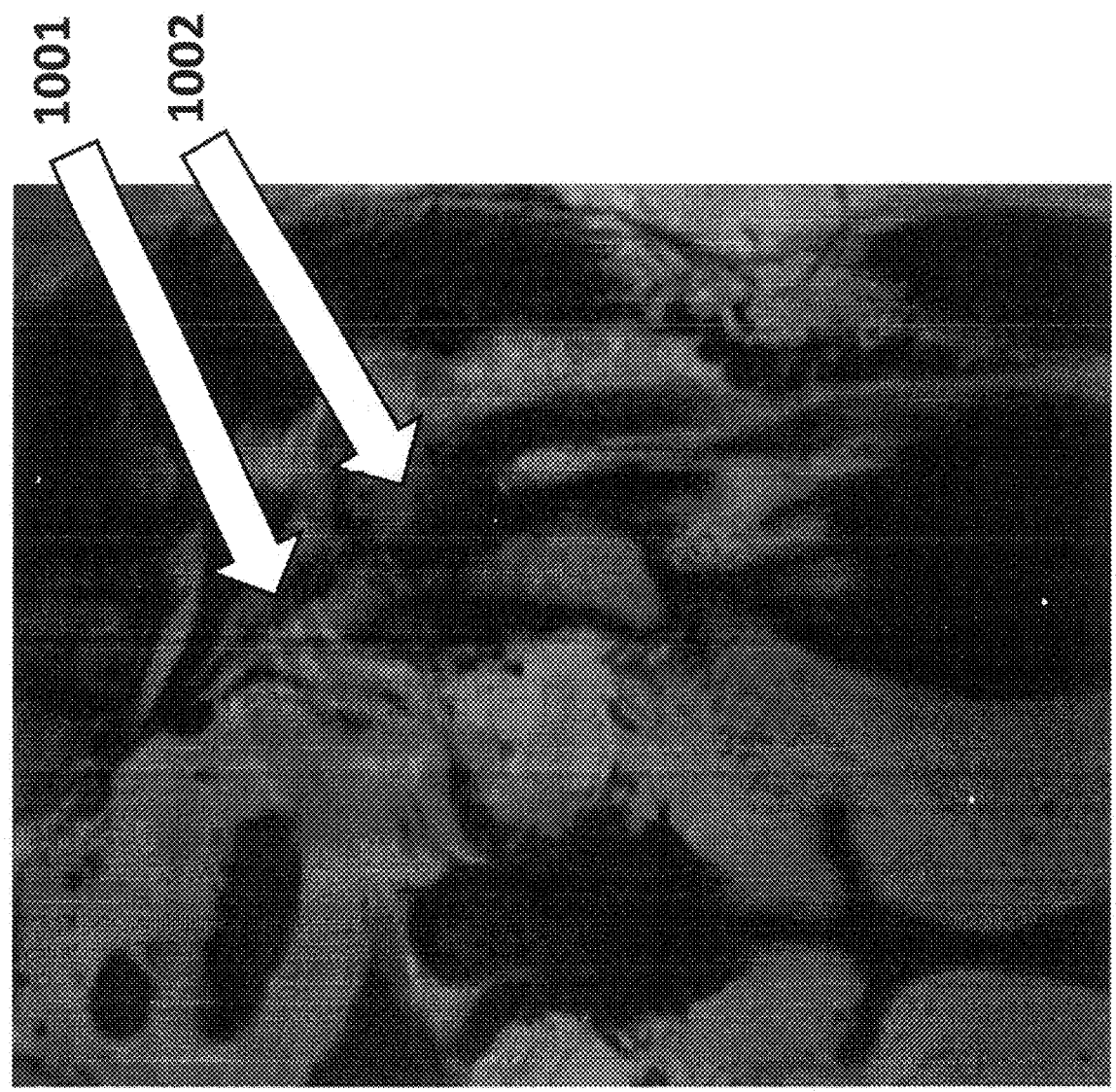

FIG. 10 depicts a magnetic resonance (MRI) peripheral nerve scan of an individual with peripheral nerve injury. The white arrows 1001, 1002 depict an area of peripheral nerve damage.

FIGS. 11A and 11B depict superparamagnetic particles forming linear structures in the presence of an externally applied magnetic field. In FIG. 11A: magnetic particles 1101 are not aligned because there is no external magnetic field (H=0). In FIG. 11B: magnetic particles align to form fibers 1102 when an external horizontal magnetic field is present.

Figure 12:
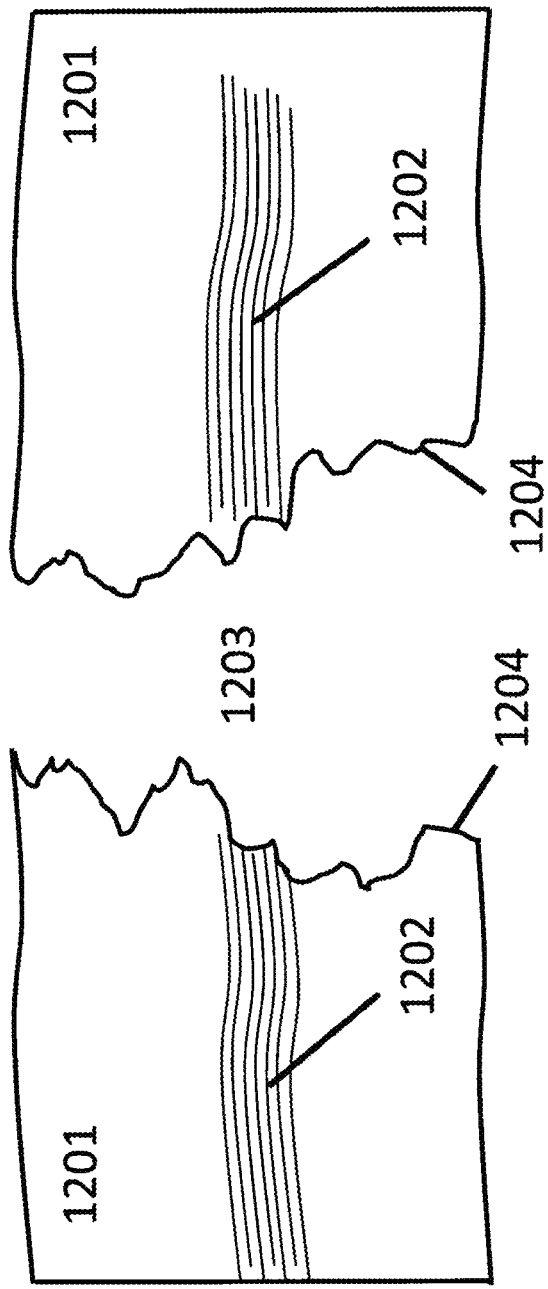

FIG. 12 depicts a neural lesion injury environment 1203 following peripheral nerve, spinal cord, or cortical circuit nervous system injury with an irregularly shaped lesion site 1204 between the two ends of damaged nerve 1202.

Figure 13:
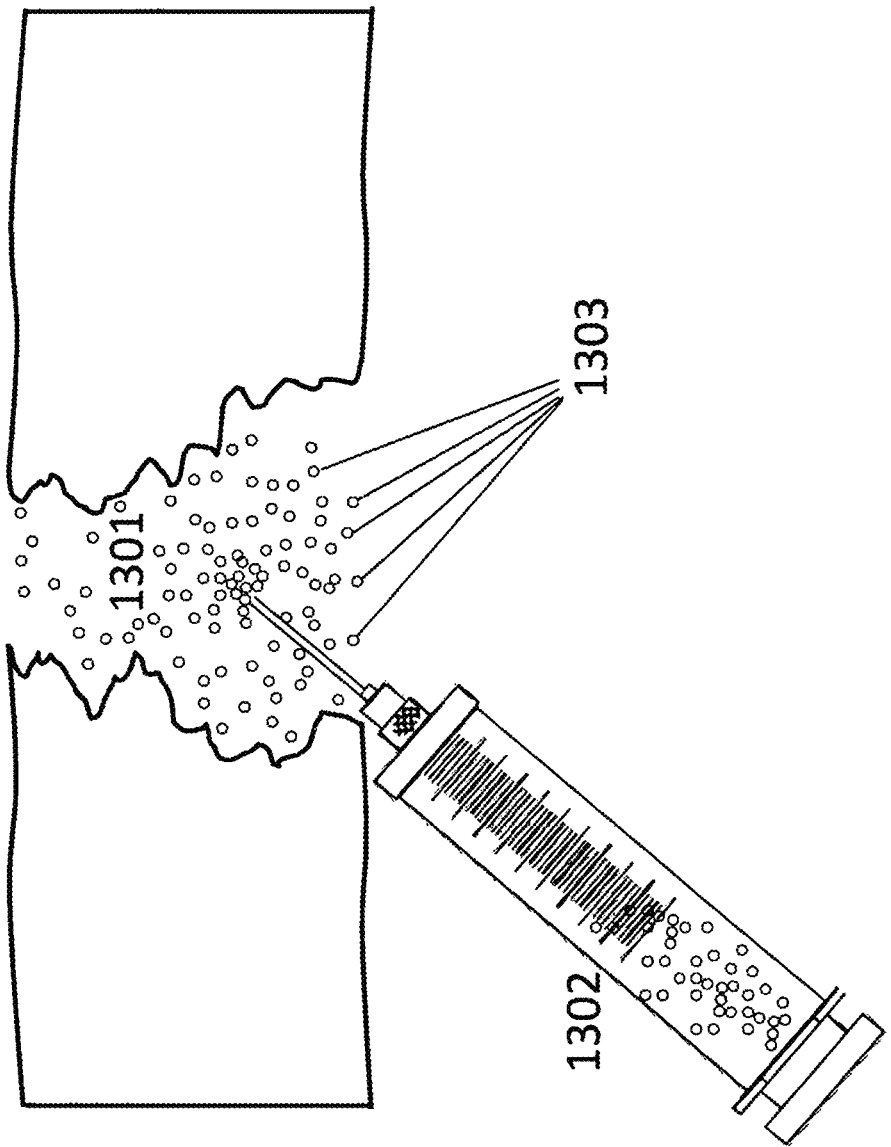

FIG. 13 depicts a formulation 1303 of the present invention being injected into an irregularly shaped lesion site 1301 between the two ends of a damaged nerve using a syringe 1302.

Figure 14:
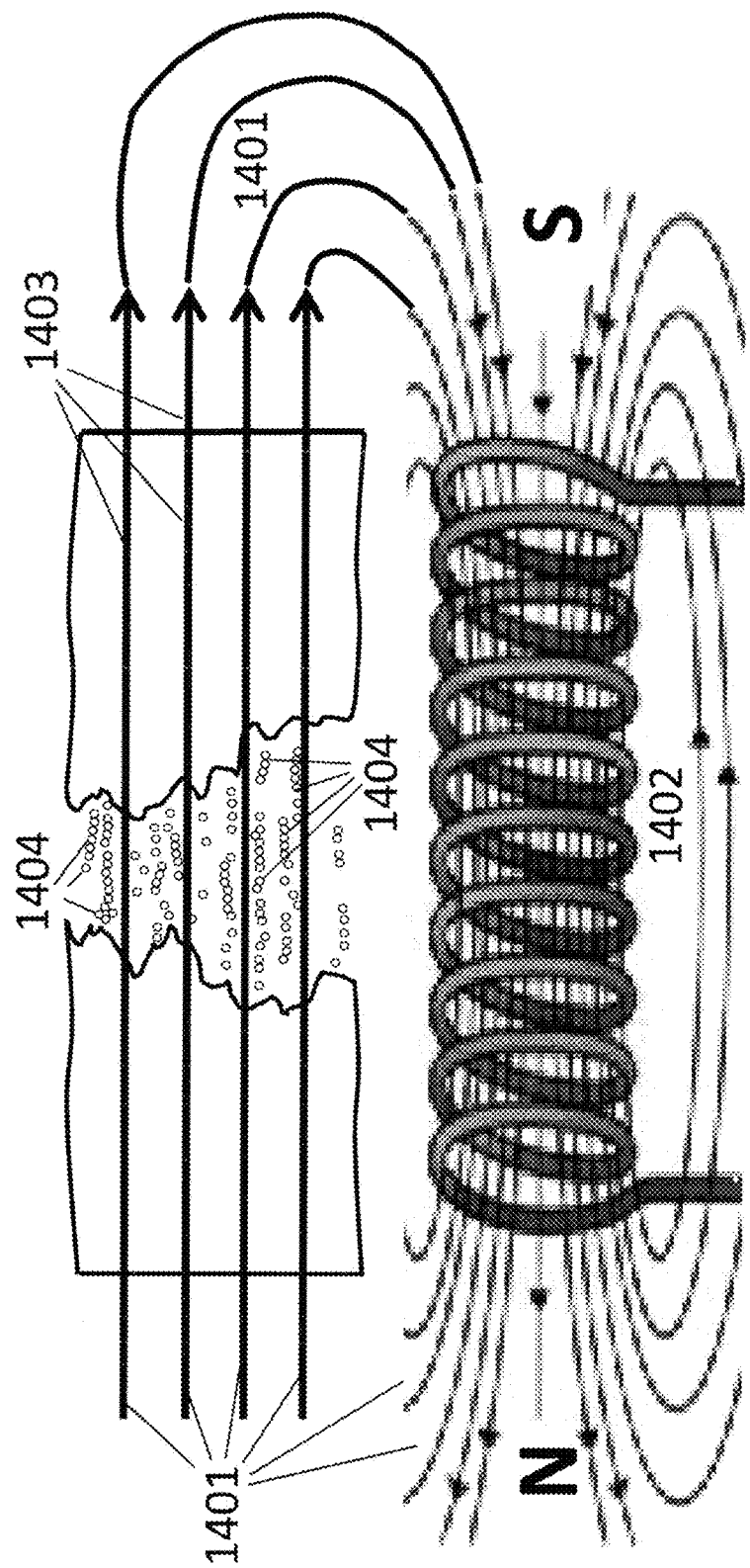
Figures 19A, 19B, 19C, 19D:
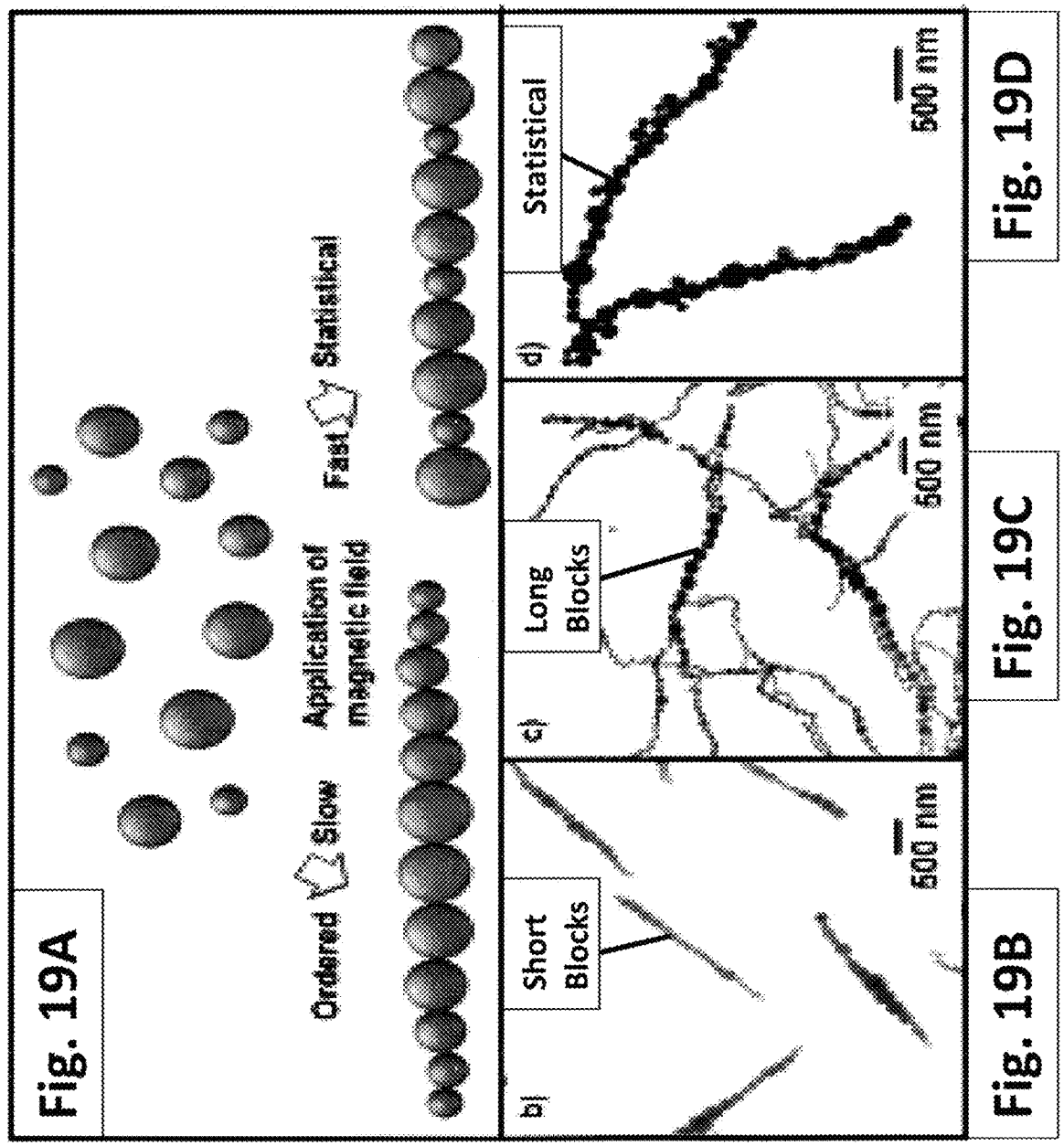

FIG. 14 depicts the process of orientation and linear alignment of magnetic particles present in the injected formulation along the field lines of an externally applied magnetic field, forming a scaffold.

FIG. 15 depicts a completed scaffold formation of linearly aligned magnetic particles 1503 of the injected formulation along the field lines of a now absent and previously externally applied magnetic field. FIG. 15 depicts a neural lesion injury environment following spinal cord 1501 injury with an irregularly shaped lesion site between the two ends 1504 of damaged nerve 1502.

FIG. 16 depicts the injection of optional factors LM16 that enhance and guide directional nerve growth into the center plane of the lesion, indicated by line 1601.

FIG. 17 depicts an in vitro model developed to test the extension of nerve cells along aligned electrospun magnetic fibers, demonstrating the ability of magnetic fibers to guide neurites 2 mm into a hydrogel.

FIGS. 18A, 18B, 18C depict uses of colloidal building blocks to form polymers of different lengths, different sequences and different degrees of branching.

FIGS. 19A, 19B, 19C, 19D depict uses of a magnetic field to create polymers which are short blocks, long blocks or statistical in structure.

FIGS. 20A, 20B, 20C, 20D, 20E depict uses of a magnetic field and crosslinking to create magnetic particle-based scaffolds which remain stable due to crosslinking despite the absence of a magnetic field. In FIG. 20A, magnetic particles 2001 assemble into a fiber of magnetic particles 2002 which in presence of sol-gel 2003 creates gel-coated magnetic particle fibers 2004. FIG. 20B depicts in a highly schematic form magnetic particles 2005 that are randomly positioned in the absence of an external magnetic field, but presence of an external magnetic field causes formation of magnetic particle fibers 2007 along the orientation of the magnetic field (H). Following crosslinking by amidation, magnetic particle fibers 2009, which are crosslinked, maintain their orientation despite absence of magnetic field. In FIG. 20C, a scanning electron microscope image of individual magnetic particles 2006 is shown. FIG. 20D provides image of magnetic particle fibers 2008 aligned along the orientation of the magnetic field. FIG. 20E provides image of amidatively crosslinked magnetic particle fibers 2010 maintaining their orientation despite absence of magnetic field.

DETAILED DESCRIPTION OF THE INVENTION

Figure 1:
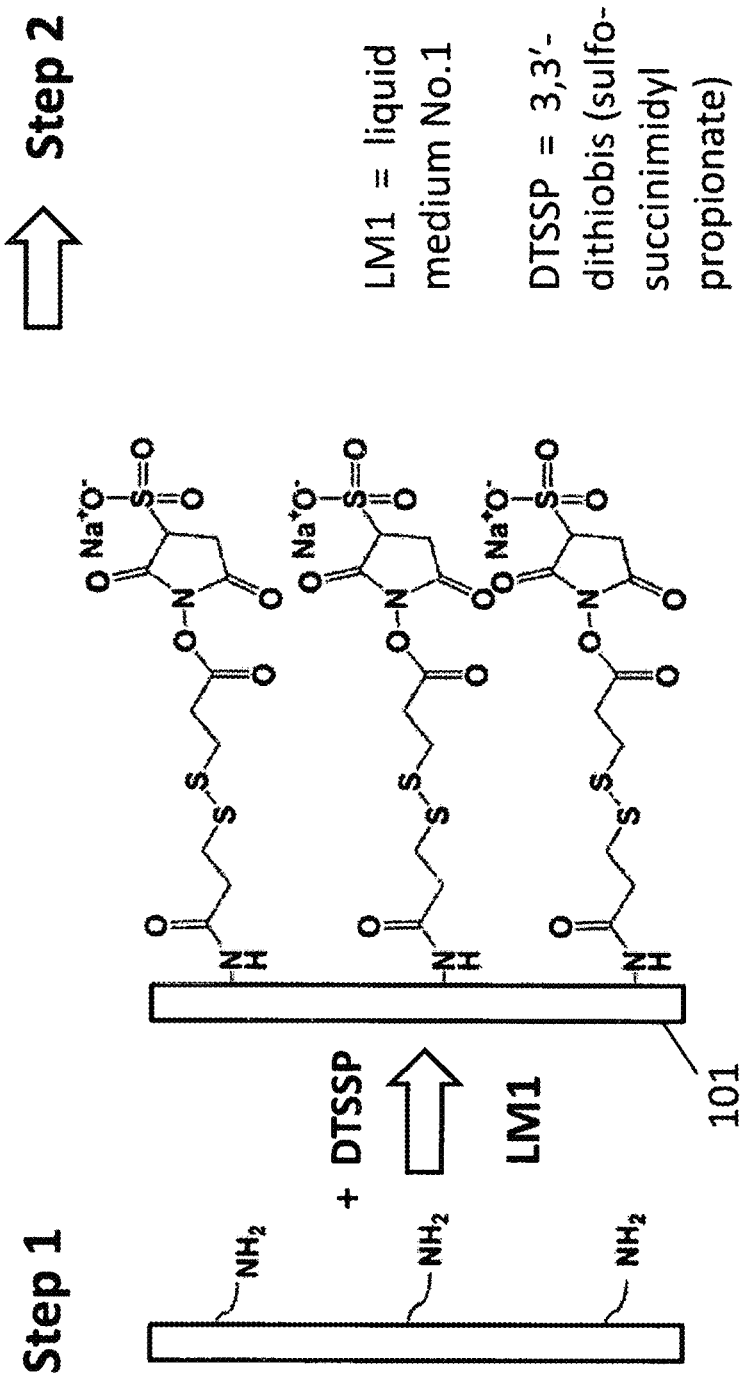
FIG. 1 depicts Step 1, the preparation of an immobilized thiol reagent on a surface, of a process for chemical group functionalization duringthe manufacture of a magnetic field sensitive Janus particle.

FIG. 1 depicts Step 1, the preparation of an immobilized thiol reagent on a surface, of a process for chemical group functionalization during the manufacture of a magnetic field sensitive Janus particle. In Step 1, the liquid medium 1 is preferably water at pH 7.2-8.5, and the DTSSP is 3,3'-dithiobis(sulfo-succinimidyl propionate) which is a water soluble thiol reagent. An amide bond forms between a thiol reagent DTSSP and a primary amine of a flat surface 101. This amidation immobilizes the DTSSP to flat surface 101. The immobilized amidated thiol reagent is then used in step 2. This amidation immobilizes the DTSSP to flat surface 101. The immobilized amidated thiol reagent is then used in Step 2.

Figure 2:
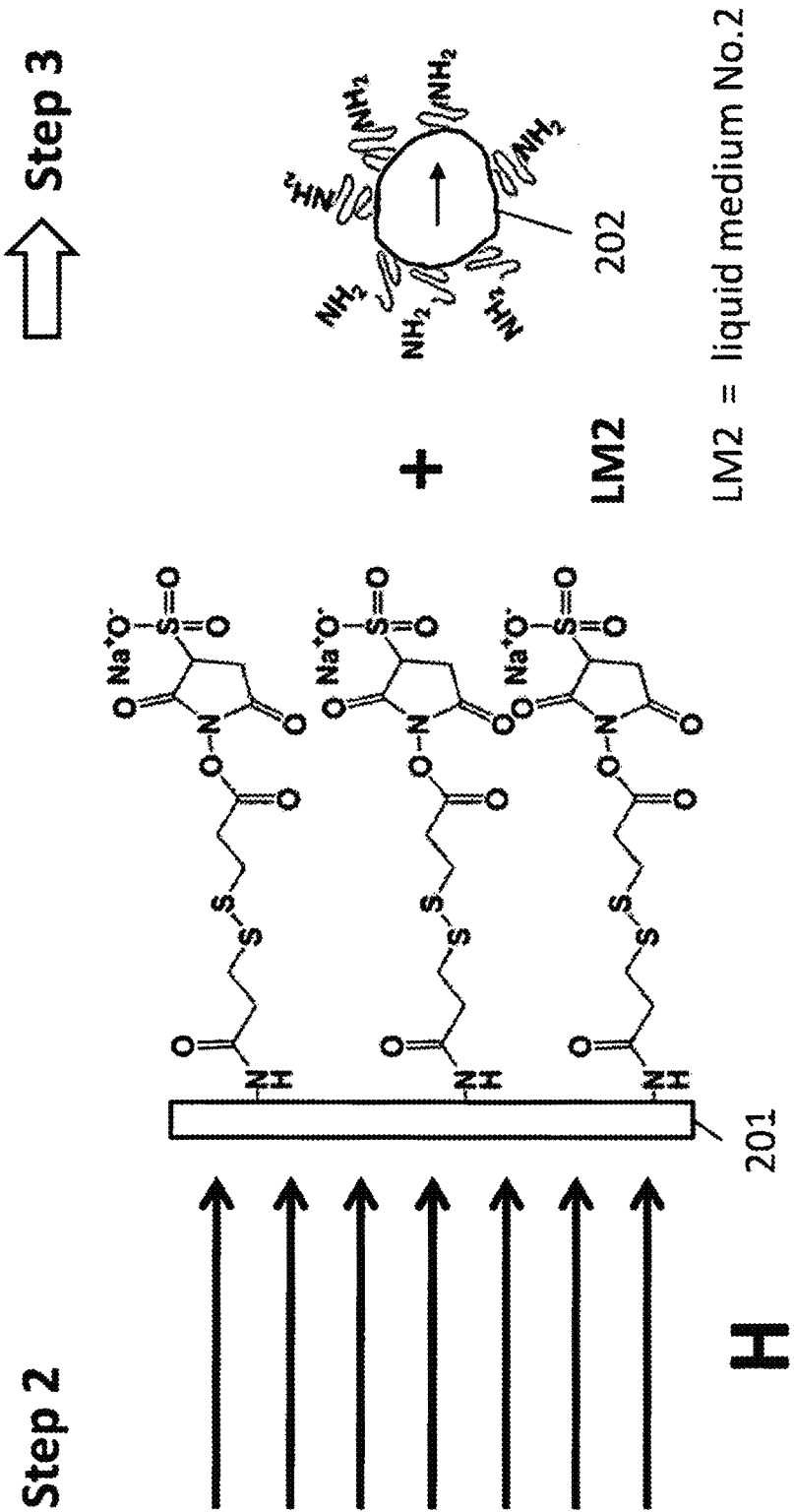
FIG. 2 depicts Step 2, leading to the preparation of magnetically oriented particles, of a process for chemical group functionalization during the manufacture of a magnetic field sensitive Janus particle.

FIG. 2 depicts Step 2, leading to the preparation of magnetically oriented particles, of a process for chemical group functionalization during the manufacture of a magnetic field sensitive Janus particle. In Step 2, a uniform magnetic field H is imposed perpendicular to the surface 201 on which is the immobilized amidated thiol reagent DTSSP from Step 1 in LM1. In this example LM1 and LM2 are the same liquid medium which is preferably water at pH 7.2-8.5. Primary amine functionalized superparamagnetic particles 202 in LM2 are added to the surface 201 with immobilized amidated thiol reagent DTSSP covered in LM1. The primary amine functionalized superparamagnetic particle 202 magnetic moment is depicted by the arrow on the particle. Primary amine functionalized superparamagnetic particles 202 can be purchased of a selected diameter. Superparamagnetic particles 202 are not perfectly round but in the imposed uniform H magnetic field perpendicular to surface 201 advantageously develop a magnetic moment parallel in alignment to the imposed uniform magnetic H field regardless of their imperfection in roundness. The primary amine functionalized superparamagnetic particle 202 magnetic moment is depicted by the arrow on the particle. The mixture of Step 2 in the magnetic field H is then used in Step 3 depicted in FIG. 3.

Typical magnetic field strengths sufficient to orient the superparamagnetic particles range from 5 mT (milli Tesla) to 500 mT. A magnetic field strength for orienting the superparamagnetic particles may be selected from the group consisting of range 5 mT (milli Tesla) to 500 mT, 1 mT to 20 mT, 10 mT to 100 mT, 15 mT to 150 mT, 100 mT to 1000 mT, 500 mT to 5000 mT or a combination thereof. The magnetic field strengths to orient the superparamagnetic particles can for example, be generated by one or more suitable permanent magnets or by electromagnets that are situated underneath, above or both underneath and above the surface 201 on which the particles are to be oriented by the magnetic field. If the magnet (or multiple magnets, as described below) are not placed in direct vicinity (i.e. typically between 1-10 mm, or between 10-50 mm distant) to the magnetic particles that are to be oriented, then magnets with a correspondingly stronger core field strength are used to generate sufficient field strength and orientation at the site where the magnetic particles that are to be oriented (i.e. on the surface during manufacture or at the lesion site when used in a composition to treat a patient). Suitable magnetic fields can for example be generated by permanent magnets or electromagnets that are placed underneath, above or both underneath and above the surface on which the particles are to be oriented. An example of a suitable electromagnet that creates field strengths on the order of tens of mT is a ten layer copper coil with 125 windings per layer and a height of 20 cm (i.e. from Magnetech Corporation, AEC Magnetics, Tasharina Corp, Essentra PLC). A preferred assembly for the surface-based manufacture of magnetically aligned Janus-type particles is a stacked composite of two electromagnets facing each other with a gap spacer (i.e. MFG-6-12 by Magnetech Corporation) that generates magnetic flux lines perpendicular to the diameter test area. The gap distance (i.e. the maximum height of the test area) is set by gap spacers. Magnetic field strengths can be measured with commercially available magnetometers, such as MPMS XL from Quantum Design, USA. Higher field strengths on the order of hundreds of mT and greater are readily achieved by commercially available permanent magnetic separators (Generation Biotech, Qiagen, New England BioLabs, Thermofisher, Promega, MoBiTec, Germany) or rare earth or neodymium magnets (Supermagnete, Germany). Permanent magnets with residual magnetism field strengths of 500 mT-2 T are commercially readily available in various shapes and sizes suitable for the present invention. Permanent or electromagnets can also be placed individually or in groups in locations not directly underneath of above the surface as long as their resulting magnetic field in the location of the surface is oriented in the desired (in this case perpendicular) orientation. Additionally, non-permanent magnetizable materials (i.e. ferromagnetic materials, such as soft iron) of a shape that conforms the magnetic field created by permanent or electromagnets can be placed in suitable locations to influence, rectify, concentrate or direct the magnetic field lines into a desired orientation.

FIG. 3 depicts Step 3, the thiolytic cleavage of magnetically oriented Janus particles from a surface, of a process for chemical group functionalization during the manufacture of a magnetic field sensitive Janus particle. In Step 3, a uniform magnetic field H is imposed perpendicular to the surface 201 on which is the immobilized amidated thiol reagent DTSSP in LM1. While in the uniform magnetic field H, the primary amine functionalized superparamagnetic particle 202 from Step 1 in LM2 reacts with the carbonyl carbon of the sulfo-succinimidyl propionate of the immobilized thiol reagent to form an amide which is held on the flat surface 201. Then addition of dithiotheitol (DTT) in liquid medium 3 (LM3) which is pH 7.0-8.0 water causes thiolytic cleavage of the disulfide bond in the immobilized amidated thiol reagent DTSSP to surface 201. The primary amine functionalized superparamagnetic particle now is a Janus particle with a Side A which has thiol (—SH) group functionalization, and with a Side B which has a primary amine functionalization. After cleavage, each particle's intrinsic magnetic moment remains aligned with functionalized Sides A and B when an external magnetic field is present. The now formed Janus (thiol Side A-amine Side B) functionalized superparamagnetic particle is in aqueous liquid medium 3 (water at pH 7-8).

Optionally, the Janus functionalized superparamagnetic particle remains in the uniform magnetic field, but in any event is then next used in Step 4. Additional stabilizing ingredients may include dithiothreitol (DTT) with a pH 7-8 pH buffer to prevent disulfide formation between two or more Janus functionalized superparamagnetic particles. Examples of stabilizing liquid medium 4 (LM4) are: pH 7-8 buffered water with dithiothreitol (DTT) or a dithiol which is a faster acting aqueous pH 7 disulfide reducing agent such as (N,N'dimethyl-N,N'-bis(mercptoacetyl) hydrazine (DMH), bis(2-mercaptoethyl)sulfone (BMS), meso-2,5-dimercapto-N,N,N',N'-tetramethyladipamide (DTA).

The Janus functionalized superparamagnetic particles can be frozen, lyophilized, or freeze-dried to minimize Janus particle chemistry that depends on an aqueous liquid medium or room temperature to clump the particles. Other molecules can be added to slow Janus functionalized superparamagnetic particle collisions such as a salt or a sugar, or a polyethylene glycol, The FIG. 3 Step is readily scaled up using a microfluidics device (see U.S. Pat. No. 6,720,143, Genetic assay system; U.S. Pat. No. 6,585,939, Microstructures for use in biological assays and reactions; U.S. Pat. No. 6,225,109, Genetic analysis device). Note that the size of the magnetic particles used in Peiris (2011) is large (100 micron diameter) relative to CNS axons which are 0.75 to about 20 microns in diameter. Therefore, we prefer to buy and use primary amine functionalized superparamagnetic particle which are 0.5 to 10 microns diameter to follow the protocol by Peiris (2011) but carry it out on a flat surface, such as in a microfluidic reaction chamber that repeatedly gets flushed and refilled to enable higher throughput production of the particles. This scale up is not a primary concern in this example for making the Janus (thiol Side A-amine Side B) functionalized superparamagnetic particle. Note that the size of the magnetic particles used in Peiris (2011) are large (100 micron diameter) relative to CNS axons which are 0.75 to about 20 microns in diameter. Therefore, we prefer to buy and use primary amine functionalized superparamagnetic particle which are 0.5 to 10 microns diameter to follow the protocol by Peiris (2011) but carry it out on a flat surface, such as in a microfluidic reaction chamber that repeatedly gets flushed and refilled to enable higher throughput production of the particles. This scale up is not a primary concern in this example for making the Janus (thiol Side A-amine Side B) functionalized superparamagnetic particle. However, note that for us the surface 201 is preferably flat, or oriented to be perpendicular to the external magnetic field. In contrast, in the Peiris (2011) protocol, the surface 201 is a column of large particles on which the synthesis is carried out (with the surface functional groups oriented in any direction. However, note that for us the surface 201 is preferably flat, or oriented to be perpendicular to the external magnetic field. In contrast, in the Peiris (2011) protocol, the surface 201 is a column of large particles on which the synthesis is carried out with the surface functional groups oriented in any direction. FIG. 4 depicts Janus (thiol Side A-amine Side B) functionalized superparamagnetic particles in a stabilizing liquid medium 4 (LM4) in the absence of an external magnetic field. The particles are able diffuse and rotate in LM4 and their internal magnetic moment can fluctuate. Preferably the superparamagnetic Janus functionalized particles have an average diameter in an aqueous isotonic saline medium (AISM) selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination of diameters thereof. Examples of stabilizing liquid medium 4 (LM4) are: pH 7-8 buffered water with dithiothreitol (DTT) or a faster acting disulfide reducing agent such as (N,N'dimethyl-N,N'-bis(mercpto-acetyl) hydrazine (DMH), bis(2-mercaptoethyl) sulfone (BMS), meso-2,5-dimercapto-N,N,N',N'-tetramethyladipamide (DTA). FIG. 5 depicts Janus (thiol Side A-amine Side B) functionalized superparamagnetic particles in a stabilizing liquid medium 5 (LM5) in the presence of an externally applied magnetic field as used during treatment. The particles and their internal magnetic moments are confined in their rotation and align with the externally applied magnetic field.

The particles, their surface functionalizations (for example Side A and Side B, See FIG. 4) and their internal magnetic moment (arrows inside the particles) consistently resume a parallel orientation in the presence of an externally applied magnetic field (H). The formulation comprising these particles in liquid medium 5 LM5 is injected into the lesion of the patient. The magnetic field H is applied either immediately following the injection of the formulation or is already present during administration of the formulation. FIG. 5 depicts a time immediately (i.e. 0-2 minutes, as well as 2-10 minutes) following the injection of the formulation when the particles have assumed their parallel orientation along the external magnetic field but have not yet formed chains and linear fibers. FIG. 6 depicts proximity-based, non-directional crosslinking of functionalized superparamagnetic particles in a stabilizing liquid medium 6 (LM6), forming linear and crosslinked structures in the presence of an externally applied magnetic field.

Particles with homogenous (non-Janus type) surface functionalizations that allow for proximity-based, non-directional crosslinking form structures in an externally applied magnetic field that may include clustered and branched aggregates. The degree of formation of such aggregates versus purely linear chain formation can be controlled by additives provided in liquid medium 6, LM6. FIG. 7 depicts Janus (Side A-Side B) functionalized superparamagnetic particles in a stabilizing liquid medium 7 (LM7) forming improved, linear, Janus-type crosslinked, single-stranded chains and structures in the presence of an externally applied magnetic field.

Figure 8:
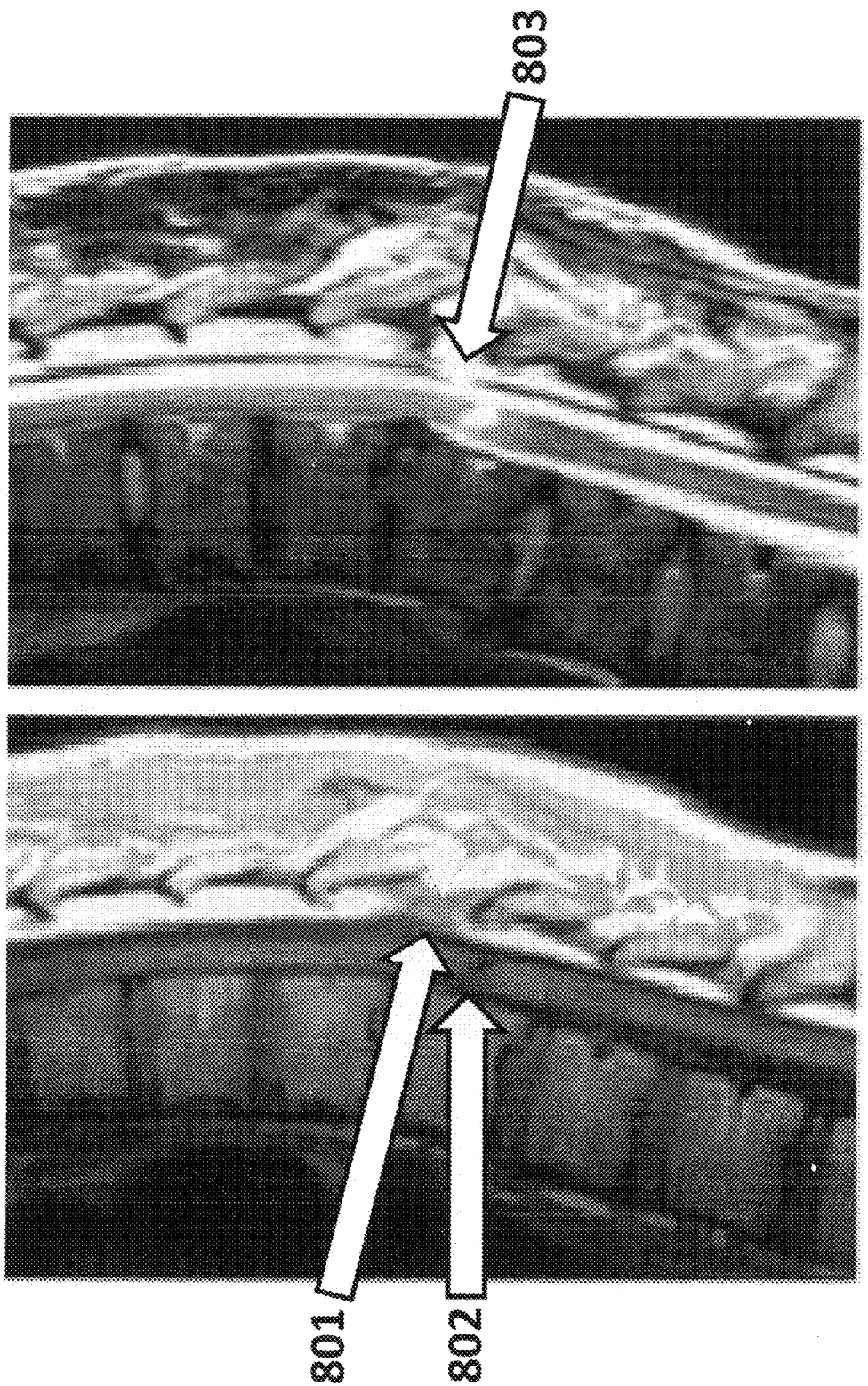

Particles with proximity- and orientation-based crosslinking form more linear, single-stranded chains compared to particles that undergo non-directional crosslinking. On top of FIG. 7 a chain is depicted that consists of particles that have two different functionalizations on their left (Side A) versus their right (Side B), as illustrated in FIGS. 3, 4, 5. On the lower half of FIG. 7 a second chain of the same type is depicted but without showing the particle surface functionalization. Non-functionalized magnetizable particles are optionally added to minimize undesirable degrees of non-linear crosslinking. Non-directed self-assembly of Janus particles into chains can optionally also be achieved without an externally applied magnetic field. FIG. 8 depicts magnetic resonance (MRI) images of a contusive spinal cord injury (open white arrow) from Chaundra (2012). A): T1W (T1-weighted image); B): T2W (T2-weighted image). Tears of the flaval ligaments (black arrowhead) and posterior dura (open black arrow) are also present. The formulation is injected into the injury site to help direct the regeneration of neural tissue. FIG. 9 depicts a magnetic resonance (MRI) brain scan of an individual with traumatic brain injury. The holes (black) depict regions of damage. Large injury sites are depicted using white arrows.

MRI brain scan of an individual with traumatic brain injury (Johnson, 2016). The holes (black) depict regions of damage. Large injury sites are depicted using white arrows. The formulation is injected into lesion domains to facilitate regeneration of neural circuits. FIG. 10 depicts a magnetic resonance (MRI) peripheral nerve scan of an individual with peripheral nerve injury. The white arrows depict an area of peripheral nerve damage.

MRI peripheral nerve scan of an individual with peripheral nerve injury (Thawait, 2012). The white arrows depict an area of peripheral nerve damage. The formulation is injected into the lesion site to facilitate directed axonal regeneration of the injured peripheral nerve. FIG. 11 depicts superparamagnetic particles forming linear structures in the presence of an externally applied magnetic field. A): magnetic particles are not aligned in the absence of an external magnetic field (H=0). B): magnetic particles align to form fibers with an external horizontal magnetic field present.

The particles in the formulation are optionally paramagnetic, superparamagnetic or ferromagnetic and reorient themselves in response to an externally applied magnetic field. When the field is applied, the internal magnetic moment of the particles is amplified and gets aligned with the external magnetic field direction, which leads to a mutual attraction between neighboring magnetic particles that results in their linear alignment along the field lines (FIGS. 6, 7, 11). The magnetic interaction between the particles eventually results in the formation of extended chains of magnetic particles in the direction of the field lines (FIG. 14). Examples of suppliers of suitable superparamagnetic particles are: Generation Biotech, Bangs Laboratories, Inc., Merck KGaA/MilliporeSigma, Thermofisher/Dynabeads. FIG. 12 depicts a neural lesion injury environment following peripheral nerve, spinal cord, or cortical circuit nervous system injury with an irregularly shaped lesion site between the two ends of damaged nerve.

FIG. 12 depicts an injury environment following peripheral nerve, spinal cord, or cortical circuit nervous system injury with an irregularly shaped lesion site between the two ends of damaged nerve. Uninjured tissue (1201) consists of gray matter or white matter found in the brain or spinal cord. In the peripheral nervous system, peripheral nerve consists of aligned fascicles consisting of individual axons. Myelinated axons are severed (1202). The immune reaction to the injury causes further cell death and cavitation of the injury site. The resulting irregularly shaped injury site (1203) is commonly observed in traumatic brain injury, contusive spinal cord or contusive peripheral nerve injury. Reproducing the aligned architecture of axons (1202) is a promising method for treatment of nervous system injury. In both the central and peripheral nervous system, mechanical insult initiates cell death and increases the size of the injury. Neural injuries can be small (millimeters in scale) or some neural injuries can span several centimeters (1204). FIG. 13 depicts a formulation of the present invention being injected into an irregularly shaped lesion site between the two ends of a damaged nerve using a syringe.

FIG. 13 represents a depiction of damaged neural tissue, either damaged brain, spinal cord, or peripheral nerve injury (1301). The formulation is injected into an irregularly shaped lesion site between the two ends of a damaged nerve using a syringe (1302) directly into the injury site. The formulation contains magnetic particles (1303) randomly distributed throughout the lesion cavity as a result of the injection. formulation magnetic particles may comprise bound or adsorbed adhesive molecules that are supportive of axonal regeneration (central and peripheral), Schwann cell migration (peripheral), astrocyte migration (central), oligodendrocyte (central), and endothelial cell/smooth muscle cell migration (peripheral and central). Such adhesion molecules include the amino acid sequence RGD (supporting cell adhesion of all cell types), IKVAV (supporting neural adhesion/extension), and or YIGSR (supporting neural adhesion/extension); laminin (supporting neural adhesion/extension) and/or L1 (supporting neural adhesion and extension); fibronectin and/or vitronectin (supporting general cell adhesion). The formulation fills the irregular geometry of the lesion site, allowing for the formulation (and resulting solidified hydrogel) to inherently match the unique geometry of any irregularly shaped lesion. FIG. 14 depicts the process of orientation and linear alignment of magnetic particles present in the injected formulation along the field lines of an externally applied magnetic field, forming a scaffold.

FIG. 14 depicts the process of orientation and linear alignment of magnetic particles present in the injected formulation along the field lines of an externally applied field forming a scaffold as previously illustrated in FIGS. 5, 6 and 7. After injection into the lesion cavity (FIG. 13), the formulation containing the magnetic particles is subjected to an externally applied magnetic field (1401) that is generated through the use of a permanent magnet or electromagnet (1402) such that magnetic field lines (1403) that transverse the lesion cavity are oriented parallel to the direction of the desired cellular regeneration, which is horizontal in this case. As a result, the magnetic particles present in the formulation form fibers (1404) comprising the magnetic particles (see also FIGS. 6 and 7) that follow the magnetic field lines.

Typical magnetic field strengths to affect the orientation and linear alignment of magnetic particles range from 5 mT (milli Tesla) to 500 mT. They can be generated by permanent magnets or electromagnets that are placed underneath, above, both underneath and above, or around the lesion cavity in which the particles are to be oriented. Suitable electromagnets are available from Magnetech Corporation, AEC Magnetics, Tasharina Corp, or Essentra PLC. If the magnet (or multiple magnets, as described below) are not placed in direct vicinity (i.e. typically between 1-10 mm, or between 10-50 mm distant) of the magnetic particles that are to be oriented in the lesion cavity, then magnets with a correspondingly stronger core field strength are used to generate an external magnetic field of sufficient strength and correct orientation at the lesion site.

Magnets producing field strengths of 100 mT-2 T are commercially available (Generation Biotech, Qiagen, New England BioLabs, Thermofisher, Promega, MoBiTec, Germany, Supermagnete, Germany). Permanent or electromagnets can be placed individually or in groups in locations not directly underneath of above the lesion cavity so that their resulting magnetic field across the lesion cavity is oriented in the desired orientation (i.e. parallel to the direction of intended nerve growth). Additionally, non-permanent magnetizable materials (i.e. ferromagnetic materials, such as soft iron) of a shape that conforms the magnetic field created by permanent or electromagnets can temporarily be placed in suitable locations outside or inside the patient's body to influence, rectify, concentrate or direct the magnetic field lines across the lesion cavity into the desired orientation.

It is desirable that the externally applied magnetic field is essentially homogeneous across the lesion cavity and does not contain any significant field gradients that would result in an undesirable translational movement and concentration of the particles and particle-formed chains towards the highest field strength. For the purposes of this invention any lateral movement of particles or particle-formed chains is neither required nor desired, except for their linear alignment across the lesion cavity along the field lines of the external magnetic field.

The formulation optionally further comprises other components, such as cells, nerve cells or stem cells, that aid in neurite re-growth and regeneration, and further optionally comprises cell growth factors, proteins, signaling molecules or chemicals that stimulate or aid in the growth, adhesion, proliferation of certain cells, in particular the directional growth of cells, such as nerve cells. Their function is to help guide axonal regeneration along the preferred direction in order to reconnect and repair the damaged nerve endings after a lesion. The formulation further optionally comprises a carrier for the controlled, retarded, extended or slow release of such compounds, such as porous particles, gels, capsules etc. as known in the art. These components of the formulation are embedded in a biocompatible liquid matrix with a viscosity suitable to be injected into the lesion cavity by syringe.

The assembly of particles into polymer-like architectures is generally challenging and usually requires highly defined colloidal building blocks. However, particles can be assembled into a simple, linearly aligned architecture under an externally applied magnetic field. They can subsequently then be permanently linked by various processes to form a desired guiding scaffold across the lesion cavity that persists indefinitely even in the absence of the initially applied external magnetic field. Examples for controllable processes for reversibly or irreversibly linking magnetic particles to each other or additional entities that are present in the matrix formulation or the lesion itself are:

Crosslinking or polymerization through chemical, biochemical or biological moieties or reactants such as psoralen, epoxy, amine, methyl methacrylate, bonds involving cognate binding partners such as avidin, streptavidin, antibodies, antigens, ligands, biotin, fluorescein, DNA hybridization, DNA origami, DNA dendrimers, aptamers, protein-protein binding, protein-DNA binding, metal chelators, Ni(2+)-NTA (nitrilotriacetic acid), His-tags, polyethylene glycol (PEG)-linkers, pH change Functionalized superparamagnetic particles are utilized extensively for the purification of cells and biomolecules, such as antibodies, nucleic acids, and polypeptides. The particles are commercially available in a wide range of sizes, magnetic content and moments, encapsulations, coatings and chemical surface modifications that are readily customized with functional molecules, chemical groups and cognate binding partners suitable for polymerization, crosslinking or linear chain formation, such as: silica, NH2, SH, COOH, CHO, C18-C4, target-specific ligands or antibodies, DNA, RNA, LNA, PNA, tosyl, biotin, streptavidin, protein A, protein G, fibrinogen, thrombin, collagen, riboflavin Physical means such as swelling by application of heat, shrinking by application of heat, magnetic hyperthermia, electrical heating, thermal sintering, ultrasound, pressure, shear force, molecular entanglement, topological locking, gel-formation from agarose, acrylamide, collagen.

A variety of architectures can be realized by controlling factors such as the nature of the particles, their surface functionalization (comprising either a single or multiple functional entities or ligands), their concentration, their order of addition to a mixture or matrix, their junction points via a size-dependent self-assembly of the building blocks, and the nature, duration, strength, variability, frequency, homogeneity, gradient and temporal application pattern of an externally applied magnetic field.

FIG. 15 depicts a completed scaffold formation of linearly aligned magnetic particles of the injected formulation along the field lines of a now absent and previously externally applied magnetic field.

After continued application of an external magnetic field to the formulation, the magnetic particles form extended fibers that follow the orientation of the external magnetic field. Once the desired degree of particle orientation is achieved, the matrix component of the formulation is allowed to solidify or cross-link into the desired 3D-scaffold, thereby locking the oriented particles into place without the continued need for an externally applied magnetic field. Crosslinking formulations may comprise fibrinogen with thrombin to create a fibrin hydrogel (peripheral nerve and central nerve applications), collagen hydrogel (peripheral nerve applications), and/or peptide-modified polyethylene glycol (PEG) hydrogel (peripheral nerve and central nerve applications). FIG. 16 depicts the injection of optional factors that enhance and guide directional nerve growth into the center plane of the lesion, indicated by line (a).

Optional factors can be administered to desired locations that further enhance and guide the directional growth, migration, and extension of regenerating axons, blood vascular cells (endothelial cells, smooth muscle cells), and glial cells (astrocytes, Schwann cells, and oligodendrocytes). Within the formulations, proteins or drugs may be loaded either within the formulation itself or delivered from polymer spheres or fibers (consisting of poly-L-lactic acid, polyglycolic acid, and/or polycaprolactone) to affect inflammation or scarring, which include the cytokines interleukin-4, interleukin-10 and/or other neuroprotective molecules including erythropoietin, minocycline, and/or estrogen. Additionally, the formulation consists of appropriate growth factors either within the formulation itself or released from polymer spheres for extended release. These factors include (NGF), brain derived growth factor (BDNF), ciliary neurotrophic factor (CNTF), neurotrophin-3 (NT-3), glial derived growth factor (GDNF), and/or vascular endothelial growth factor (VEGF). The formulation may comprise stromal cell derived factor-1 alpha (SDF-1alpha) to encourage the migration of endogenous neural stem cells into the lesion site following traumatic brain injury. Generally, growth factor inclusion would reduce neuronal cell loss, spur axonal regeneration, encourage angiogenesis, and Schwann cell migration (peripheral), astrocyte migration (central), and oligodendrocyte migration (central). The formulation may also comprise cells supportive of nervous tissue regeneration including autologous (bone marrow derived) and/or allogenic (human umbilical cord) mesenchymal stem cells, autologous induced pluripotent stem cells. An example of a desirable location is the center plane of the lesion, indicated by line (a) in FIG. 16. Such factors may be embedded in slow-release carrier vehicles. FIGS. 17A, 17B, 17C depict an in vitro model developed to test the extension of nerve cells (neurites) 1707 along aligned magnetic electrospun fibers 1701. In FIG. 17A, top panel, aligned magnetic electrospun fibers 1701 are depicted in a magnified view. In FIG. 17A, middle panel 1702, depicted is a Dorsal Root Ganglion (DRG) 1706 with neurites 1707 growing along the aligned magnetic electrospun fibers. In FIG. 17A, lower panel 1703, depicted is a Dorsal Root Ganglion (DRG) 1706 with neurites 1707 growing 2 mm along the aligned magnetic electrospun fibers in a fluorescence view, demonstrating the ability of magnetic fibers to guide neurites 1707 into a hydrogel that contains 6% weight superparamagnetic iron oxide nanoparticles per weight of the poly-1-lactic acid polymer (referred to as: 6% nanoparticle fibers) 1701. In FIG. 17B (histogram 1704), neurite alignment parallel to the orientation of the fibers is greater than 50%. The neurite alignment is measured by the angle that the neurites deviate from the primary angle of orientation of the fibers to show how well the neurites align with the 6% nanoparticle fibers. The angle deviation measurements are compiled into a histogram to show the distribution of neurites that extend at certain angles. The graphs represent 4 independently fabricated fibers and 4 DRG isolated from different rats. The alignment histogram 1704 shows that the neurites that contacted the fibers (black bars) align along the fibers and only deviate from the fiber alignment (set to 0 degrees) by ±20 degrees. The neurites that are not in contact with the fibers do not have a preferred axis of orientation and deviate ±180 degrees (gray bars). The alignment histogram 1704 shows that the neurites that interact with the aligned fibers are highly aligned, while those that are not in contact with the aligned fibers are not aligned. In FIG. 17C (bar graph 1705), the length of neurites growing into the fibers averages 2 mm, whereas in the hydrogel the length is less than 1 mm. The benefit of this aligned growth is also seen when the neurite length is measured. The neurites that grow along the aligned fibers grow an average of 2 mm into the scaffold, a significant increase (t-test, $p<0.05$) over the length of the neurites which grow into the hydrogel alone. In total, FIGS. 17A, 17B and 17C indicate that neurites grow longer and more aligned in an in vitro model when an aligned topography (6% nanoparticle Fibers) is provided to guide the neurites. The 6% nanoparticle fibers are encapsulated in a 10 milligrams fibrin/milliliter water with a 1:100 dilution of Growth Factor Reduced PRF Matrigel and cultured for 5 days in growth media (50 ng/ml Neural Growth Factor, 1% penicillin/streptomycin, 10% heat inactivated horse serum, 89% Dulbecco's Modified Essential Medium). Dorsal Root Ganglia (DRG) are commonly used as a model for neurite outgrowth after injury to the nervous system because DRG are positioned in the body so the DRG interact with both the central and peripheral nervous system. DRG also have a similar growth response to injured neural tissue, with many neurites extending out of the body of the DRG after transplant. Primary DRG are surgically isolated from Sprague Dawley rats, and positioned in the biomaterial (aligned 6% nanoparticle electrospun fibers encapsulated in a fibrin/Matrigel hydrogel) in vitro so that one half of the DRG contacts the aligned fibers, and the other half contacts the hydrogel only 1702. In this way, the neurites extending from the DRG into the hydrogel act as a control response for neurite outgrowth of the other half of the DRG body that is extending into the aligned structure.

A phase contrast image of this model is depicted in (1702), and the same DRG is fluorescently labeled (immunocytochemistry) for neurofilament—a neuron specific marker in the image below (1703). Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

The invention discloses a method of regenerating a nerve fiber in a damaged neural tissue of a patient, the method comprising the steps of:

administering an aqueous formulation comprising superparamagnetic particles to the damaged neural tissue in the patient; applying a magnetic field in an orientation which is parallel to the nerve fiber; using the magnetic field for aligning the superparamagnetic particles; forming one or more aligned chains of the superparamagnetic particles in the magnetic field as a scaffold to guide directional growth of regenerating nerve cells; and reconnecting damaged nerve ends in the damaged neural tissue of the patient.

The invention further discloses an earlier step of functionalizing surfaces of the superparamagnetic particles with one or more chemical moieties prior to administering the aqueous formulation comprising the superparamagnetic particles to the damaged neural tissue in the patient, wherein the surfaces of the superparamagnetic particles are functionalized with the one or more chemical moieties selected from the group consisting of a carbohydrate, a protein, a lipid, a glass, an oligosaccharide, a peptides, a laminin, a biotin, an avidin, a streptavidin, a DNA hybridization molecule, a cross-linking agent, a thiol, a sulfide, an oxide, a sulfhydryl, a sulfide, a disulfide, a sulfinyl, a sulfoxide, a sulfonyl, a sulfone, a sulfinic acid, a sulfino, a sulfonic acid, a sulfo, a thioketone, a carbonothioyl, a thial, a primary amine, a secondary amine, a tertiary amine, a carboxylate, a carboxyl, an alkoxy, a hydroperoxy, a peroxy, an alkyl, an alkene, an alkyne, an aryl derivative, a halo group, a hydroxyl, a carbonyl, an aldehyde, an acyl halide, an ester, a carbonate ester, an ether, a hemi-acetal, a hemiketal, a ketal, an orthoester, a methylenedioxy, a cycloalkyl, a heterocyclic, a heteroaryl, an orthocarbonate ester, a carboxamide, a primary ketimine, a secondary ketamine, a primary aldimine, a secondary aldimine, an imide, a nitro, a phosphonic acid, a phosphate, a phosphodiester, a nitrile, an isonitrile, an isocyanate, an antibody, a pharmaceutical excipient, a pH buffer, a cerium oxide nanoparticle, a manganese dioxide nanoparticle, EDTA, EGTA, NTA, HEDTA, a cytokine, and a combination thereof.

The invention further discloses wherein the earlier step of functionalizing the surfaces of the superparamagnetic particles with the one or more chemical moieties is for promoting a chemical bonding between the superparamagnetic particles when the magnetic field is aligning the superparamagnetic particles and forming the one or more aligned chains of the superparamagnetic particles parallel to the nerve fiber.

The invention further discloses wherein the earlier step of functionalizing the surfaces of the superparamagnetic particles with the one or more chemical moieties is for forming Janus superparamagnetic particles.

The invention further discloses wherein the functionalized Janus superparamagnetic particles have a Side A surface functionalized with a first chemical moiety and have a Side B surface functionalized with a second chemical moiety.

The invention further discloses wherein the earlier step of functionalizing the surfaces of the superparamagnetic particles with the one or more chemical moieties for forming the Janus superparamagnetic particles is conducted in the presence of a magnetic field.

The invention further discloses wherein the functionalized Janus superparamagnetic particles have the Side A surface functionalized with the first chemical moiety as a thiol and have the Side B surface functionalized with the second chemical moiety as a primary amine.

The invention further discloses wherein the functionalized Janus superparamagnetic particles have the Side A surface functionalized with the first chemical moiety as a carboxylic acid and have the Side A surface functionalized with the second chemical moiety as a primary amine.

The invention further discloses wherein the aqueous formulation comprising the superparamagnetic particles further comprises a molecule selected from the group consisting of a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4-sulfation on astrocyte-derived chondroitin sulfate proteoglycan, an inhibitor of chondroitin sulfate proteoglycan phosphacan, an inhibitor of chondroitin sulfate proteoglycan neurocan, a chondroitinase-ABC, an inhibitor of chondroitin sulfate proteoglycan 4, an inhibitor of neuron-glial antigen 2, an antibody to chondroitin sulfate proteoglycan 4, an antibody against neuron-glial antigen 2, an inhibitor of glial cell expression of chondroitin sulfate proteoglycan 4, an inhibitor of glial cell expression of neuron-glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI-35, an antibody against myelination inhibitory factor NOGO, an anti-oxidants, cerium oxide nanoparticles, an amino acid, a phospholipid, a lipid, a vitamin, an anticoagulant, and a combination thereof.

The invention further discloses wherein the aqueous formulation comprising the superparamagnetic particles further optionally comprises a carrier which is microspheres, porous particles, a gel, a hydrogel, a multiphase solution, a colloid, a capsule, a microcapsule, a liposome, an isotonic saline, a cerebrospinal fluid, or a combination thereof.

The invention further discloses the step of stabilizing the aligned chains of the superparamagnetic particles in the magnetic field using a cross-linking polymer architecture for locking the aligned chains of the superparamagnetic particles into place after the step of using the magnetic field for aligning the superparamagnetic particles in the orientation which is parallel to the nerve fiber orientation in the damaged neural tissue and forming the one or more aligned chains of the superparamagnetic particles in the magnetic field in the orientation which is parallel to the nerve fiber orientation in the damaged neural tissue, and before the step of using the one or more aligned chains of the superparamagnetic particles in the orientation which is parallel to the nerve fiber orientation in the damaged neural tissue as a scaffold for regenerating the nerve fiber in the damaged neural tissue of the patient. In some invention method embodiments, the aligned chains of the superparamagnetic particles that are the scaffold for regenerating the nerve fiber in the damaged neural tissue of the patient are stabilized by a cross-linking polymer architecture.

The invention further discloses wherein the cross-linking polymer architecture for stabilizing the aligned chains of the superparamagnetic particles is selected from the group consisting of a cross-linking homopolymer of the surface functionalized superparamagnetic particles, a cross-linking copolymer of different surface functionalized superparamagnetic particles, a cross-linking junction controlled branched polymer of the surface functionalized superparamagnetic particles, and a combination thereof.

The invention further discloses wherein the cross-linking polymer architecture for stabilizing the aligned chains of the superparamagnetic particles is formed using molecules selected from the group consisting of psoralen, methyl methacrylate, avidin, streptavidin, antibodies, antigens, ligands, biotin, laminin, fluorescein, DNA hybridization molecules, DNA origami, DNA dendrimers, aptamers, protein-protein binding, protein-DNA binding, metal ion chelators, His-tags, polyethylene glycol-linkers, agarose, acrylamide, collagen, phase transfer catalysts, and any combination there.

The invention further discloses the step of removing the magnetic field which is parallel to the nerve fiber orientation after the step of stabilizing the aligned chains of the superparamagnetic particles using the cross-linking polymer architecture.

The invention further discloses wherein the superparamagnetic particles have dimensions selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination thereof.

The invention further discloses wherein the magnetic field has a strength between about 5 milli Tesla to about 500 milli Tesla.

The invention further discloses wherein the damaged neural tissue of the patient is in the spinal cord of the patient.

The invention further discloses wherein the damaged neural tissue of the patient is in the peripheral nervous system of the patient.

The invention further discloses wherein the cross-linking polymer architecture for stabilizing the aligned chains of the superparamagnetic particles is formed using molecules selected from the group consisting of avidin, streptavidin, biotin, laminin, DNA hybridization molecules, and any combination thereof.

The invention further discloses an earlier step of a healthy section of the neural tissue from the patient into an area of the damaged neural tissue of the patient prior to the step of administering the aqueous formulation comprising the superparamagnetic particles to the damaged neural tissue area in the patient.

Definitions Section

1. A neurite or neuronal process refers to any projection from the cell body of a neuron and the projection can be an axon or a dendrite. The term neurite or neuronal process is frequently used when speaking of immature or developing neurons, especially of cells in culture, because it can be difficult to tell (fully functional, i.e. electrical impulse conducting) axons from dendrites before differentiation is complete.

2. Neuroregeneration and the regeneration of nervous tissue refer to the regrowth or repair of nervous tissues, cells or cell products. Such mechanisms may include generation of new neurons, glia, axons, myelin, or synapses. Neuroregeneration differs between the peripheral nervous system (PNS) and the central nervous system (CNS) by the functional mechanisms and especially the extent and speed. When an axon is damaged, the distal segment undergoes Wallerian degeneration, losing its myelin sheath. The proximal segment can either die by apoptosis or undergo the chromatolytic reaction, which is an attempt at repair. In the CNS, synaptic stripping occurs as glial foot processes invade the dead synapse. The nervous system is divided into two parts: the central nervous system, which consists of the brain and spinal cord, and the peripheral nervous system, which consists of cranial and spinal nerves along with their associated ganglia. While the peripheral nervous system is observed to have an intrinsic ability for repair and regeneration, the central nervous system appears based on current understandings, to be incapable of self-repair and regeneration. This lack of understanding will be replaced by awareness of the factors necessary for CNS regeneration. Neuroregeneration is important clinically, as it is part of the pathogenesis of many diseases, including multiple sclerosis.

3. Neuroregeneration in the peripheral nervous system (PNS) refers to a number of processes. In the PNS, axonal sprouts form at the proximal stump and grow until they enter the distal stump. The growth of the sprouts is governed by chemotactic factors secreted from Schwann cells (neurolemmocytes). Injury to the peripheral nervous system immediately elicits the migration of phagocytes, Schwann cells, and macrophages to the lesion site in order to clear away debris such as damaged tissue. When a nerve axon is severed, the end still attached to the cell body is labeled the proximal segment, while the other end is called the distal segment. After injury, the proximal end swells and experiences some retrograde degeneration, but once the debris is cleared, it begins to sprout axons and the presence of growth cones can be detected. The proximal axons are able to regrow as long as the cell body is intact, and they have made contact with the Schwann cells in the endoneurial channel or tube. Human axon growth rates can reach 1 mm/day in small nerves and 5 mm/day in large nerves. The distal segment, however, experiences Wallerian degeneration within hours of the injury; the axons and myelin degenerate, but the endoneurium remains. In the later stages of regeneration the remaining endoneurial tube directs axon growth back to the correct targets. During Wallerian degeneration, Schwann cells grow in ordered columns along the endoneurial tube, creating a band of Büngner (boB) that protects and preserves the endoneurial channel. Also, macrophages and Schwann cells release neurotrophic factors that enhance re-growth.

4. Inhibitory influences of the glial and extracellular environment in the CNS refers to processes which suppress spontaneous recovery of the CNS from CNS injury. The hostile, non-permissive growth environment is, in part, created by the migration of myelin-associated inhibitors, astrocytes, oligodendrocytes, oligodendrocyte precursors, and microglia. The environment within the CNS, especially following trauma, counteracts the repair of myelin and neurons. Growth factors are not expressed or re-expressed; for instance, the extracellular matrix is lacking laminins. Glial scars rapidly form, and the glia actually produce factors that inhibit remyelination and axon repair; for instance, NOGO and NI-35. The axons themselves also lose the potential for growth with age, due to a decrease in GAP 43 expression. Slower degeneration of the distal segment than that which occurs in the peripheral nervous system also contributes to the inhibitory environment because inhibitory myelin and axonal debris are not cleared away as quickly. These factors contribute to the formation of what is known as a glial scar, which axons cannot grow across. The proximal segment attempts to regenerate after injury, but its growth is hindered by the environment. Central nervous system axons regrow in permissive environments. Thus, one of the major problems to central nervous system axonal regeneration is crossing or eliminating the inhibitory lesion site.

5. Glial scar formation refers to processes induced following damage to the nervous system. In the central nervous system, glial scar formation inhibits nerve regeneration, which leads to a loss of function. Several families of molecules are released that promote and drive glial scar formation. For instance, transforming growth factors B-1 and -2, interleukins, and cytokines play a role in the initiation of scar formation. The accumulation of reactive astrocytes at the site of injury and the up regulation of molecules that are inhibitory for neurite outgrowth contribute to the failure of neuroregeneration. The up-regulated molecules alter the composition of the extracellular matrix in a way that has been shown to inhibit neurite outgrowth extension. This scar formation involves several cell types and families of molecules.

6. Chondroitin sulfate proteoglycan refers to a group of molecules involved in glial scar formation. In response to scar-inducing factors, like those discussed above, astrocytes up regulate the production of chondroitin sulfate proteoglycans. Astrocytes are a predominant type of glial cell in the central nervous system that provide many functions including damage mitigation, repair, and glial scar formation. The RhoA pathway is involved. Chondroitin sulfate proteoglycans (CSPGs) are up regulated in the central nervous system (CNS) following injury. Repeating disaccharides of glucuronic acid and galactosamine, glycosaminoglycans (CS-GAGs), are covalently coupled to the protein core CSPGs. CSPGs inhibit regeneration in vitro and in vivo. GAG profiles of normal cortex and glial scar tissue differ. Glial scar tissue demonstrated an up regulation of chondroitin-4, 6-sulfate, chondroitin-2-sulfate, and chondroitin-6-sulfate. On the other hand, uninjured cortical tissue contains mostly CS-GAG which comprises chondroitin-4-sulfate, chondroitin, and chondroitin-6-sulfate. CSPGs inhibit neurite outgrowth. However, CS-E and aggrecan are the most inhibitory and contain mostly 4,6-sulfated GAG and 4-sulfated GAG. A large increase in 4-sulfated chondroitin occurs after injury to the spinal cord and selective increases or decreases of the 4-sulfation on astrocyte-derived chondroitin sulfate proteoglycans have growth promoting or growth inhibiting actions, respectively. Thus 4-sulfation is believed to be a factor in modification of CSPGs in the glial scar. The chondroitin sulfate proteoglycans phosphacan and neurocan have also been shown to play a role in glial scar. Phosphacan has been shown to have decreased levels in glial scar when compared to uninjured cortex. This decrease is beneficial to nerve generation because phosphacan has been shown to inhibit neurite extension similarly to the other CSPGs discussed already. Alternatively, neurocan production is up regulated in astrocytes in glial scar when compared to uninjured cortex and astrocytes in primary cell culture conditions. These elevated neurocan levels have been found 30 days after the initial injury. This implicates neurocan as having a prolonged role in chronic scar. NG2 is another type of chondroitin sulfate proteoglycan that is expressed by oligodendrocyte precursor cells.

7. Oligodendrocyte precursor cells refer to another type of glial cell found in the central nervous system that play a role in glial scar formation. These cell types can develop into a normal oligodendrocyte or a glial fibrillary acidic protein positive astrocyte depending on environmental factors. NG2 is found on the surface of these cells and has been shown to inhibit neurite outgrowth extension, as well. These are high molecular weight transmembrane molecules with the largest portion extending into the extracellular space. Following injury to the central nervous system, NG2 expressing oligodendrocyte precursor cells are seen around the site of injury within 48 hours of the initial injury. The number of NG2 expressing cells continues to increase for the next three to five days and high levels of NG2 are seen within seventen days of the injury. NG2 inhibits neurite growth inhibition. On substrates containing both NG2 and adhesive molecules, neurite extension is reduced more than compared to neurite extension on substrates only containing the adhesive molecules. The accumulation of NG2 expressing cells at the site of injury creates an extracellular barrier that inhibits axon regrowth into the glial scar area.

8. Oligodendrocyte refers to a neuroglial cell similar to an astrocyte but with fewer protuberances, concerned with the production of myelin in the central nervous system equivalent to the function performed by Schwann cells in the peripheral nervous system. The myelin sheath, which is 80% lipid and 20% protein. A single oligodendrocyte can extend its processes to 50 axons, wrapping approximately 1 µm (micrometer) of myelin sheath around each axon. A Schwann cell wraps around only one axon. Each oligodendrocyte forms one segment of myelin for several adjacent axons.

9. Keratan sulfate proteoglycans refer to molecules which are like the chondroitin sulfate proteoglycans, in that keratan sulfate proteoglycan (KSPG) production is up regulated in reactive astrocytes during glial scar formation. KSPGs have also been shown to inhibit neurite outgrowth extension, limiting nerve regeneration. Keratan sulfate, also called keratosulfate, is formed from repeating disaccharide galactose units and N-acetylglucosamines. It is also 6-sulfated. This sulfation is crucial to the elongation of the keratan sulfate chain.

10. Inhibitory proteins in oligodendritic or glial debris include the following seven proteins: (1) NOGO which is an inhibitor of remyelination in the CNS; (2) NI-35 a nonpermissive growth factor from myelin; (3) MAG a Myelin-associated glycoprotein; (4) Oligodendrocyte Myelin glycoprotein; (5) Ephrin B3 which inhibits remyelination; (6) Semaphorin 4D which inhibits remyelination; and (7) Semaphorin3A present in the scar which forms in both central nervous system and peripheral nerve injuries, contributes to the outgrowth-inhibitory properties of these scars.

11. Surgical Treatments of Neural Tissue Damage are conceived to be able to benefit from various embodiments of the present invention. Surgery can be done in case a peripheral nerve has become cut or otherwise divided. This surgery is known as peripheral nerve reconstruction. The injured nerve is identified and exposed so that normal nerve tissue can be examined above and below the level of injury, usually with magnification, using either loupes or an operating microscope. If a large segment of nerve is harmed, as can happen in a crush or stretch injury, the nerve will need to be exposed over a larger area. Injured portions of the nerve are removed. The cut nerve endings are then carefully re-approximated using very small sutures. The nerve repair must be covered by healthy tissue, which can be as simple as closing the skin or it can require moving skin or muscle to provide healthy padded coverage over the nerve. Recovery after surgical repair of a divided peripheral nerve depends mainly on the age of the patient as young children can recover close-to-normal nerve function. In contrast, a patient over 60 years old with a cut nerve in the hand can expect to recover only protective sensation; that is, the ability to distinguish hot/cold or sharp/dull. Another recovery factor is what caused the injury. For example, a sharps injury such as a knife wound, damages only a very short segment of the nerve and needs just a direct suture. In contrast, nerves that are divided by stretch or crush may be damaged over long segments. These nerve injuries are more difficult to treat and generally have a poorer outcome. In addition, associated injuries, like injury to bone, muscle and skin, can make nerve recovery more difficult. The distance for nerve regeneration is a well-known problem and limitation to regeneration of neural tissue following neural tissue damage. For example, a nerve injured at the wrist that normally provides sensation to the thumb must grow to the end of the thumb in order to provide sensation. The return of function decreases with increased distance over which a nerve must grow.

12. Autologous nerve grafting refers to a nerve autograft used to repair large lesion gaps in the peripheral nervous system. Nerve segments are taken from another part of the body (the donor site) and inserted into the lesion to provide endoneurial tubes for axonal regeneration across the gap. Often the final outcome is only limited function recovery. Partial deinnervation is experienced at the donor site, and multiple surgeries are often required to harvest nerve tissue for additional nerve implant surgery. When appropriate, a nearby donor may be used to supply innervation to lesioned nerves. Trauma to the donor can be minimized by utilizing a technique known as end-to-side repair. In this procedure, an epineurial window is created in the donor nerve and the proximal stump of the lesioned nerve is sutured over the window. Regenerating axons are redirected into the stump. The efficacy of this technique is dependent upon the degree of neurectomy. The more neurectomy the greater possibility for axon regeneration within the lesioned nerve, but with the consequence of increasing nerve deficit to the donor. Some evidence suggests that local delivery of soluble neurotrophic factors at the site of autologous nerve grafting may enhance axon regeneration within the graft and help expedite functional recovery of a paralyzed target.

13. Nerve guidance conduit refers to the development of artificial nerve guidance conduits in order to guide axonal regrowth. The creation of artificial nerve conduits is also known as entubulation because the nerve ends and intervening gap are enclosed within a tube composed of biological or synthetic materials.

Thus, regeneration of neural tissues in an area with neural damage or neural lesion is a broad term relating to many complex neural recovery processes. There is rebuilding of nervous cellular electrophysiological networks between nerve cells where the nerve cells may be located in the peripheral nervous tracts or in the central nervous system. Regeneration processes, include cellular repopulation in damaged tissues, changes in differentiation of cell such as neurite growth, growth of nerve and glial cells, creation of new differentiated nervous system cells and replacement of cellular matrix, the role of stem cells which may be neural stem cells, the roles of glial cells, astrocytes, oligodendrocytes, axon regrowth, dendrite regrowth, restoration of synaptic connections, creation of new synapses, regrowth of nervous tissue vascular tissues, growth of reconnections between nerve cells, remyelination of nerves, and processes for directing or guiding new axonal growth leading to restoration or renewal of nerve cell synapses to other nerve cells.

In one embodiment of the method, the injection of an aqueous formulation of the invention into a lesion site is used to reconnect a previously damaged nerve, even after significant scar tissue has already been formed. In this embodiment, the two damaged ends of the spinal cord are surgically cut further back from the initial lesion in order to generate a 'fresh' interface of exposed nerve ends before the aqueous formulation of the invention is injected. Surgical cutting of the ends may include techniques other than using a traditional scalpel, such as mechanical, biochemical, enzymatic, chemical means that result in the abrasion, digestion, removal or exposure of 'fresh' nerve cells. Fresh means able to form neurites and connections with other nerve cells.

In a related embodiment of the present invention, additional, healthy sections of the spinal cord are deliberately sliced from one or both ends of a large lesion site. The spinal cord slices can be placed in the lesion site at distances from each other that are short enough to allow for an effective invention formulation matrix formation and neurite growth into the spaces between successive sections. In this way even very large distances of damaged or missing nerves can be successively bridged by supporting the innervation and reconnection of the neurites formed in the injected aqueous formulation of the invention with intervening sections of the original nerve. This is embodiment is similar to the technique of 'stretching' a patient's own skin, such as done for severe burn victims, when otherwise an insufficient amount of skin would be available from the patient itself to cover the entire area that requires a graft. In this technique, which is typically performed with specialized and semi-automated equipment designed for only this purpose, a certain amount of skin is first harvested from a patient and then deliberately cut with hundreds of mm-sized, alternating and parallel oriented incisions. The skin graft is then carefully stretched in the direction perpendicular to the cuts before applying it to the patient. The body of the patient is typically able to successfully attach the graft as if it were a non-treated patch of the patient's own skin because the small distance (on the order of mm) between neighboring intact sections of skin allow their epithelial cells to extend into and eventually fully fill the small open areas, just like they would do in a small cut wound. The technique is able to cover a graft of several times the area than compared to what would be able with untreated skin grafts.

14. Spinal Cord Functional Recovery refers to the fact that there currently is no cure for spinal cord injury. One challenge in achieving complete functional recovery is to develop approaches that encourage directional axonal regeneration that extends through the lesion cavity and reconnects the two severed ends of the spinal cord. The method disclosed here is not limited to the spinal cord and also applies to injuries of other types of nerves.

15. Fibrotic Glial Scar: A common problem in spinal cord injury is that within about two weeks scar tissue forms in the damaged area of the spine that prevents subsequent growth and connection of nerve cells that would be required to restore electrical conduction and functionality in the spine. Glial scar formation (gliosis) is understood to be a reactive cellular process involving astrogliosis that occurs after injury to the central nervous system. As with scarring in other organs and tissues, the glial scar is the body's mechanism to protect and begin the healing process in the nervous system.

16. Astrogliosis and astrocytosis refer to an abnormal increase in the number of astrocytes due to the destruction of nearby neurons from CNS trauma, infection, ischemia, stroke, autoimmune responses, and neurodegenerative disease. Typically it occurs over the course of several days following the injury as part of the body's normal healing mechanism. Unfortunately however this natural process ends up being counterproductive to regaining nerve function because it leads to the formation of scar-like layer that interferes with the ability of still functioning as well as newly formed neurons and neurites to reconnect the damaged or severed nerve fiber ends. One embodiment of the present invention is conceived to include removing the increased layer of astrocytes and other cells to expose a 'fresh' layer of neurons to enhance regeneration by a formulation of the present invention treating neural tissue damage.

17. Astrocyte refers to a star-shaped glial cell of the central nervous system that is related to microglia which are glial cells derived from mesoderm that function as macrophages (scavengers) in the central nervous system and form part of the reticuloendothelial system. Astrocyte proportion varies by region and ranges from 20% to 40% of all glia. Astrocytes perform many supportive functions, including biochemical support of endothelial cells that form the blood-brain barrier, provision of nutrients to the nervous tissue, maintenance of extracellular ion balance, and a role in the repair and scarring process of the brain and spinal cord following traumatic injuries. Astrocytes propagate intercellular $Ca2+$ waves over long distances in response to stimulation, and, similar to neurons, release transmitters (called gliotransmitters) in a $Ca2+$-dependent manner. Astrocytes also signal to neurons through $Ca2+$-dependent release of glutamate.

18. Hydrogel refers to a water-based gel achieved by any one of a variety of means. There are many biocompatible materials available that are used to cure or form certain shapes in the body. A short-peptide-based hydrogel matrix is capable of holding about one hundred times its own weight in water. A hydrogel may be a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Some hydrogels have the ability to sense changes of pH, temperature, or the concentration of metabolite and release a substance they are carrying and can act as a sustained-release drug delivery system. Some hydrogels are comprised of cross-linked polymers such as polyethylene oxide, polyAMPS and polyvinyl pyrrolidone (PVP). Wound gels can help create or maintain a moist environment. Hydrogel ingredients may include polyvinyl alcohol, sodium polyacrylate, acrylate polymers and copolymers with an abundance of hydrophilic groups. Natural hydrogel materials are being investigated for tissue engineering; these materials include agarose, methylcellulose, hyaluronan, and other naturally derived polymers.

19. Scaffold refers to a support used in tissue engineering which can help to mimic a 3D microenvironment of cells or tissues or provide a supportive guide to aid and direct neural cell or neural tissue regeneration. A scaffold can include various structures such as crosslinked or non-crosslinked filaments, fibers, chains as well as branched, bifurcated or polymerized elements.

20. Paramagnetic refers to a substance which is very weakly attracted by the poles of a magnet, but not retaining any permanent magnetism.

21. Superparamagnetic refers to a form of magnetism which typically appears in ferromagnetic or ferrimagnetic nanoparticles or, depending on their composition and other factors, also in larger particles. The effect is that such particles generally (at ambient temperatures and in typical solvents and matrices, such as in water-based solutions or gels or hydrogels) do not aggregate without the presence of an external magnetic field despite the relative strength of each particle's individual magnetic moment. When an external magnetic field is applied however, the random reorientation of each particle's individual magnetic moment is suppressed and forced to align parallel to the applied field. In proximity to other particles, the particles are then able to interact consistently with the magnetic moment of surrounding particles, thereby attracting each other to form parallel oriented chains and clusters. This property is highly desirable for many chemical and biochemical processes and surface chemistries where the particles are to be kept in solution until a magnetic field is applied.

22. Superparamagnetic Janus functionalized particles refers to particles with an average diameter in an aqueous isotonic saline medium (AISM) selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination of diameters thereof. Nanoparticles is a term which typically refers to a particle size or diameter of up to one micrometer, but which has been known to range widely from between about 1 nanometer to tens of thousands of nanometers. Thus, for the present invention the term nanoparticle does not impose a specific size range but indicates the particles may be submicron diameter in most cases.

23. Magnetic field for the present invention typically refers to portions of a magnetic field without a magnetic field gradient, in which case the particles, chains and clusters do not experience a macroscopic translational force that will move them to the location of the strongest field (i.e. the place where a magnet is applied). If the external field does not have a gradient, the only movement of the particles is generated as a direct effect of their own internal magnetic moment and its effects on the moment of surrounding particles. The result is that the particles move towards each other (i.e. in the direction of the greatest local field, which is generated by a neighboring particle's magnetic moment) until they contact each other. This formation of chains and clusters further amplifies the local field, thereby resulting in a more effective recruitment of additional particles to form longer and larger chains. In the absence of an external magnetic field gradient the chains and clusters remain in the (macroscopic) location of where they originated. This magnetic field dependent behavior of particles is a preferred behavior for some embodiments of the present invention. It is also possible to rotate magnetic particles in a rotating, preferably homogeneous, magnetic field. Independent of the Néel relaxation of their internal magnetic moment, the magnetic particles may also reorient themselves as a whole to adjust to the changing orientation of an externally applied magnetic field, or to the effect of the magnetic moment of a neighboring particle.

For the present invention, the selected magnetic field strengths is designed to orient the superparamagnetic particles range from 5 mT (milli Tesla) to 500 mT. If the magnet (or multiple magnets, as described below) are not placed in direct vicinity (i.e. typically between 1-10 mm, or between 10-50 mm distant) to the magnetic particles that are to be oriented, then magnets with a correspondingly stronger core field strength are used to generate sufficient field strength and orientation at the site where the magnetic particles that are to be oriented (i.e. on the surface during manufacture or at the lesion site when used in a composition to treat a patient). Suitable magnetic fields can for example be generated by permanent magnets or electromagnets that are placed underneath, above or both underneath and above the surface on which the particles are to be oriented. An example of a suitable electromagnet that creates field strengths on the order of tens of mT is a ten layer copper coil with 125 windings per layer and a height of 20 cm (i.e. from Magnetech Corporation, AEC Magnetics, Tasharina Corp, Essentra PLC). A preferred assembly for the surface-based manufacture of magnetically aligned Janus-type particles is a stacked composite of two electromagnets facing each other with a gap spacer (i.e. MFG-6-12 by Magnetech Corporation) that generates magnetic flux lines perpendicular to the diameter test area. The gap distance (i.e. the maximum height of the test area) is set by gap spacers. Magnetic field strengths can be measured with commercially available magnetometers, such as MPMS XL from Quantum Design, USA. Higher field strengths on the order of hundreds of mT and greater are readily achieved by commercially available permanent magnetic separators (Generation Biotech, Qiagen, New England BioLabs, Thermofisher, Promega, MoBiTec, Germany) or rare earth or neodymium magnets (Supermagnete, Germany). Permanent magnets with residual magnetism field strengths of 500 mT-2 T are commercially readily available in various shapes and sizes suitable for the present invention. Permanent or electromagnets can also be placed individually or in groups in locations not directly underneath of above the surface as long as their resulting magnetic field in the location of the surface is oriented in the desired (in this case perpendicular) orientation. Additionally, non-permanent magnetizable materials (i.e. ferromagnetic materials, such as soft iron) of a shape that conforms the magnetic field created by permanent or electromagnets can be placed in suitable locations to influence, rectify, concentrate or direct the magnetic field lines into a desired orientation.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Method and Compositions for Creating Magnetically Aligned Scaffolds for Tissue Regeneration—"Fibermag"

Spinal cord injury affects approximately 12,000 Americans per year and typically leads to paralysis below the injury site. Several treatments are capable of restoring some function; however there currently is no cure for spinal cord injury. One challenge in achieving complete functional recovery is to develop approaches that encourage directional axonal regeneration that extends through the lesion cavity and reconnects the two severed ends of the spinal cord. Axonal regeneration typically fails because of the formation of inhibitory fibrotic glial scar tissue at the lesion cavity within weeks after the injury, as well as due to the lack of directional guidance cues for axonal regrowth.

A fibrotic scar forms within about two weeks of the injury and leads to a cascade of secondary injury that expands and exacerbates the original lesion through ischemia, elevated calcium levels, radical formation and inflammation that lead to astrogliosis. The scar of astrocytes impedes the regrowth of neurons rather than supporting neural cells, oligodendrocytes die and the formation of new nerve cells is stopped[1].

It is therefore of critical importance to quickly fill in the injury site with a suitable, biocompatible matrix, such as a hydrogel, in order to stop scar tissue from forming. However this treatment alone does not promote axonal regeneration. It therefore is desirable to generate a 3D scaffold in a matrix with oriented conduits that can guide the neurite growth in the desired direction in order to successfully reach and connect the two respective ends of the severed cord.

Polymeric fibers with nanoscale or micro scale diameter have successfully been used to axonal regrowth in animal models of spinal cord injury. They have also been used in conjunction with biomaterials that release neurotropic growth factors and thereby further increase axonal regeneration.

Oligodendrocytes, or oligodendroglia, are a type of neuroglia that form the electrical insulation around the axons of a nerve. Their main functions are to provide support and insulation to axons in the central nervous system of some vertebrates, equivalent to the function performed by Schwann cells in the peripheral nervous system, by creating the myelin sheath. Each oligodendrocyte forms one segment of myelin for several adjacent axons. Astrocyte cells, also known as astroglia, provide biochemical support of endothelial cells that form the blood-brain barrier, provide nutrients to the nervous tissue and maintain the extracellular ion balance in addition to their role in the repair and scarring process of the spinal cord and brain following traumatic injuries.

The current state of the art however suffers from several limitations that the present invention overcomes:
1) Spinal cord lesions are often diagnosed and clearly visible by magnetic resonance imaging (MRI), yet very difficult and risky to access surgically. Minimally invasive techniques that provide equivalent or improved treatment results are therefore clearly desirable compared to traditional, open surgery.
2) The implantation of a prefabricated/3D-printed or custom-manufactured oriented fiber plug that is customized to the patient's particular lesion is a complex, time-consuming and expensive process. It requires a) an assessment and accurate three-dimensional shape determination of the void that is to be filled in the lesion cavity, b) the transfer of that information to a 3D-modeling software, c) the de-novo fabrication and/or the modification of pre-fabricated fiber plugs that should precisely match the shape of the void, and d) the surgical insertion and adjustment of this customized fiber plug. The overall process requires considerable amount of time, skill and resources. All of these resources may not be readily available during the limited time window during which reconstructive intervention of spinal cord injury can take place before scar tissue formation and other processes irreversibly close the window for a successful restoration of spinal cord function.
3) Current treatments require both highly specialized expertise and equipment which are not available in most places, be it in rural areas, other countries or in situations where competent medical help is not immediately available.

Magnetically generated, injectable scaffolding matrix for guided nerve regeneration The present invention overcomes these problems by providing a method for treating a patient of spinal cord injury with an injectable formulation, hereafter called 'Fibermag', that comprises magnetic particles and a biocompatible matrix-forming compound that can be solidified by various means in situ after its injection into the lesion of the patient, such as a spinal cord lesion cavity. The magnetic particles in the Fibermag formulation are optionally paramagnetic, superparamagnetic or ferromagnetic and reorient themselves in response to an externally applied magnetic field. When the field is applied, the internal magnetic moment of the particles is amplified and gets aligned with the external magnetic field direction, which leads to a mutual attraction between neighboring magnetic particles that results in their linear alignment along the field lines. The magnetic interaction between the particles eventually results in the formation of extended chains of magnetic particles in the direction of the field lines.

Magnetic particles are not aligned in the absence of an external magnetic field. Magnetic particles align to form fibers with external horizontal magnetic field present.

An external magnetic field is applied to the Fibermag formulation through the use of a permanent magnet or electromagnet such that the field lines are oriented parallel to the direction of the desired cellular regeneration, which is horizontal in this case. As a result, the magnetic particles that are present in the injected Fibermag formulation begin to form fibers that follow the orientation of the external magnetic field and its field lines across the lesion cavity.

After continued application of an external magnetic field to the Fibermag formulation, the magnetic particles form extended fibers that follow the orientation of the external magnetic field. Once the degree of desired particle orientation is achieved, the matrix component of the Fibermag formulation is allowed to solidify or cross-link onto the desired 3D-scaffold, thereby locking the oriented particles into place without the continued need for an externally applied magnetic field. With the desired 3D scaffold in place, optional nerve growth factors can be administered to desired locations that further enhance and guide the directional growth of regenerating nerve cells. An example of a desirable location is the center plane of the lesion. Such factors may be embedded in slow-release carrier vehicles.

It is desirable that the externally applied magnetic field is essentially homogeneous across the lesion cavity and does not contain any significant field gradients that would result in an undesirable translational movement and concentration of the particles and particle-formed chains towards the highest field strength. For the purposes of this invention any lateral movement of particles or particle-formed chains is neither required nor desired, except for their linear alignment across the lesion cavity along the field lines of the external magnetic field.

The Fibermag formulation optionally further comprises other components, such as cells, nerve cells or stem cells, that aid in neurite re-growth and regeneration, and further optionally comprises cell growth factors, proteins, signaling molecules or chemicals that stimulate or aid in the growth, adhesion, proliferation of certain cells, in particular the directional growth of cells, such as nerve cells. Their function is to help guide axonal regeneration along the preferred direction in order to reconnect and repair the damaged nerve endings after a lesion. The formulation further optionally comprises a carrier for the controlled, retarded, extended or slow release of such compounds, such as porous particles, gels, capsules etc. as known in the art. These components of the formulation are embedded in a biocompatible liquid matrix with a viscosity suitable to be injected into the lesion cavity by syringe.

The assembly of particles into polymer-like architectures is generally challenging and usually requires highly defined colloidal building blocks. However, particles can be assembled into a simple, linearly aligned architecture under an externally applied magnetic field. They can subsequently then be permanently linked by various processes to form a desired guiding scaffold across the lesion cavity that persists indefinitely even in the absence of the initially applied external magnetic field. Examples for controllable processes for reversibly or irreversibly linking magnetic particles to each other or additional entities that are present in the Fibermag matrix formulation or the lesion itself are:

Crosslinking or polymerization through chemical, biochemical or biological moieties or reactants such as psoralen, epoxy, amine, methyl methacrylate, bonds involving cognate binding partners such as avidin, streptavidin, antibodies, antigens, ligands, biotin, fluorescein, DNA hybridization, DNA origami, DNA dendrimers, aptamers, protein-protein binding, protein-DNA binding, metal chelators, Ni(2+)-NTA (nitrilotriacetic acid), His-tags, polyethylene glycol (PEG)-linkers, pH change Physical means such as swelling by application of heat, shrinking by application of heat, magnetic hyperthermia, electrical heating, thermal sintering, ultrasound, pressure, shear force, molecular entanglement, topological locking, gel-formation from agarose, acrylamide, collagen A variety of architectures can be realized by controlling factors such as the nature of the particles, their surface functionalization (comprising either a single or multiple functional entities or ligands), their concentration, their order of addition to a mixture or matrix, their junction points via a size-dependent self-assembly of the building blocks, and the nature, duration, strength, variability, frequency, homogeneity, gradient and temporal application pattern of an externally applied magnetic field.

Different polymer-like architectures that can be created by a controlled assembly and fusion of superparamagnetic particles. (a) Insertion of a monodisperse particle dispersion yields predominantly linear chains. Depending on the concentration of the particle dispersion (and the growth time), longer or shorter chains can be obtained. (b) In the case of a polydisperse sample, the differently-sized particles can self-organize into blocks of larger and smaller particles, resulting in colloidal block copolymers. A slow increase of the external magnetic field assembles the particles in a block-like pattern, a fast increase in a more statistical fashion. (c) The insertion of particles with even larger size differences enables the introduction of junction points. More than two small particles assemble around a large particle creating a junction point within the particle chain. By increasing the concentrations of particles in the dispersion, networks of cross-linked chains can be obtained.

See: Bannwarth et al., Colloidal Polymers with Controlled Sequence and Branching Constructed from Magnetic Field Assembled Nanoparticles, ACS Nano, VOL. 9' NO. 3' 2720-2728' 2015

Controlled size-self-assembly of large and small particles within a chain. (a) Schematics depicting the two possibilities to align a polydisperse sample of particles. When all particles have the same reactivity, a statistical assembly occurs. In the case of low flow rates (slow increase of the magnetic field), larger particles exhibit a higher reactivity in the early stage of the assembly process (the magnetic field is still relatively low) due to their higher magnetic content and thus their stronger response to the magnetic field. Smaller particles start to assemble later in the process (when the magnetic field strength is increased). Consequently, the larger particles assemble first followed by the assembly of smaller particles at the edges of the chain. In the case of faster flow rates, this size-dependent assembly cannot be observed since the magnetic field increase is too fast to allow for a separated assembly of large particles. Here, smaller and larger particles assemble simultaneously leading to a rather statistical size-sequencing within the chain. (b) TEM image of shorter chains of particles with the tendency to form small blocks of larger and smaller particles. Often the larger particles are found toward the middle of the chains and the smaller ones toward the ends. (c) TEM image of larger chains with large blocks of larger and smaller particles. (d) TEM image of statistically assembled particles into chains.

Magnetic particles can also be suspended in a liquid formulation and will form snake-shaped structures that can control the flow of the surrounding fluid when subjected to an alternating magnetic field. The size of these structure ranges from millimeters to a few centimeters long. Experiments show that the speed of the fluid flowing along the snake depends on how quickly the magnetic field alternates.

This effect may be utilized in a fully cross-linked/solidified Fibermag matrix to generate an internal, magnetically controlled mixing action that assists in the circulation and transport of various components that are present in the Fibermag matrix or the surrounding cellular matrix, such as cells, stem cells, nerve cells, never growth factors, vehicles for containing and releasing such factors or other drugs, hormones, inhibitors, antibiotics, cellular components, vascularization assistance factors. The matrix may optionally comprise sub-millimeter magnetic nickel particles for this purpose, which react to an alternating magnetic field created by an external electromagnetic coil. The particles align themselves head-to-tail with nearby particles as though they contain sufficiently strong internal magnetic moments. The movement of the particle chain creates waves which further encourage the formation of more parallel chains and cause a segmented pattern. The self-assembly can take anywhere from a fraction of a second to several minutes.

Numerous (bio)polymers, organic molecules and inorganic coatings have been employed in the surface modification of the magnetic structures such as poly(ethylene glycol), poly (vinyl pyrrolidone), poly(ethylene-co-vinyl acetate), poly (vinyl alcohol), dendrimers, silanes, proteins and silica. A variety of drugs such as cisplatin, methorexate, mitoxantrone, tamoxifen, danorubicin, doxorubicin and fludarabine have been loaded into the porous organic or inorganic shells of the surface-modified magnetic particles. Some of the general issues or challenges associated with the deployment of magnetic particles for drug delivery (or gene delivery) applications include (i) improving biocompatibility or obtain control over in vivo behavior, (ii) achieving control over bioelimination (which includes preventing unwanted clearance and enabling safe clearance when desired), (iii) improving specific targeting, (iv) minimizing the polydispersity (of size, surface functionality) and (v) issues related to the limited penetration of the magnetic field deep into the body Swellable and breathable materials, such as hydrogels with magnetically sensitive, embedded particles or components that can be magnetically heated, deformed, stretched, aligned, hybridized, denatured, crosslinked or disconnected, can be used to create fluidic motion and movement of the surrounding matrix scaffold with the purpose of drawing in cells from other parts of the Fibermag matrix, from outside of the matrix, from the sides of each surface of the lesion cavity where a rupture occurred, or from a blood vessel that abuts to the lesion site and the injected Fibermag matrix.

This invention relates to a method to create aligned scaffolding in situ in the body that helps specific cells such as nerve cells grow and regenerate tissue in a preferred direction.

A common problem in spinal cord injury is that within about two weeks scar tissue forms in the damaged area of the spine that prevents subsequent growth and connection of nerve cells that would be required to restore electrical conduction and functionality in the spine.

Current methods try to determine the size of the damage and create specific scaffolding outside of the patient's body. These scaffolds are complex to generate and are supposed to have a particular alignment with respect to the preferred growth direction of the nerve cells. One option currently being used is fibrous or hollow materials in which the fibers and their respective openings are aligned in a mostly parallel way according to the preferred direction in which the nerve cells are supposed to grow. The goal is to guide new nerve growth such that both ends of a severed nerve, such as in a spinal cord injury, connect. This approach suffers from serious shortcomings because it is hard to determine the exact size and dimensions of the lesion, create an appropriate insert plug and implant it in a way that is both minimally invasive but also timely enough to prevent loss of functionality to due to scar formation.

Current methods try to determine the size of the damage and create specific scaffolding outside of the patient's body. These scaffolds are complex to generate and are supposed to have a particular alignment with respect to the preferred growth direction of the nerve cells. One option currently being used is fibrous or hollow materials in which the fibers and their respective openings are aligned in a mostly parallel way according to the preferred direction in which the nerve cells are supposed to grow. The goal is to guide new nerve growth such that both ends of a severed nerve, such as in a spinal cord injury, connect. This approach suffers from serious shortcomings because it is hard to determine the exact size and dimensions of the lesion, create an appropriate insert plug and implant it in a way that is both minimally invasive but also timely enough to prevent loss of functionality to due to scar formation.

A much preferable approach is one that requires as little surgery as possible and that can be applied very quickly after an injury has occurred, after the initial swelling has abated and damage has been assessed, but before any irreversible and undesirable reconstruction and wound healing occurs that may interfere with the proper connection and regeneration of impulse conducting nerve cells.

A method that allows for rapid intervention with a simple procedure and a type of material that is biocompatible is therefore highly desirable. The present method is a treatment by injection to form a matrix inside the lesion cavity. The injected formulation forms a matrix that conforms to the size of the lesion after it has been assessed and prepared for reconstructive tissue regeneration. A sterile, biocompatible material with magnetizable particles are used to create scaffolding that guides the growth of new nerve fibers towards the right direction in order to reconnect a nerve's electrical conduction.

The invention uses a combination of externally applied magnetic fields and a suitable matrix that contains magnetic micro particles that are aligned in such a way that the magnetic field forms a scaffold from the injected material that serves to guide the growth of nerve cells into the right direction.

The particles can be magnetic, ferromagnetic, superparamagnetic nanoparticles or microparticles, with typical dimensions being 50 to 200 nanometers, 100 to 200 nanometers, 200 to 500 nanometers, 500 to 750 nanometers, 750 nanometers to 1 micrometer, 1-2 micrometers, or larger in size. The particles can be spherical or non-spherical. Elongated particles, nanorods or linked chains of particles are also desirable for this invention. Equally of interest are particles that form hollow or honeycomb-like structures when they are subjected to a magnetic field, such as particles that are linked by certain linkers known in the art, or particles that are embedded in other matrices that are orientable by an externally applied magnetic field.

The desired type of scaffold in the application for spinal cord or other nerve reconstruction is that of a longitudinally oriented, parallel scaffold that allows for the growth of the nerve cells into one direction and discourages growth directions that are in directions not parallel to the alignment of the scaffolding.

In order to initiate and enhance nerve growth into this direction, nerve growth factors, or particles or slow-release vesicles containing such nerve growth factors, can be injected and placed at specific positions in the scaffold so as to release growth factors and molecules that trigger a directed growth of the nerve cells is known in the art. For instance if two ends of the spinal cord are disconnected and the Fibermag matrix has been injected into the cavity, magnetically aligned and fixed in place (through the solidification or polymerization of a carrier matrix, such as a gel, hydrogel or another biocompatible and bio-absorbable membrane), the growth factor or compound that guides the direction of growth of the nerve cells can be locally injected at the center of the plug so as to create an incentive for the spinal cord nerve cells at each end of the inserted Fibermag matrix to grow towards the center where they reconnect and re-establish a electrically functional nerve connection.

This secondary injection will in most cases occur after the Fibermag matrix has been fully placed into the cavity and has solidified so that the injected growth factor does not freely diffuse to places where there is no nerve growth target intended.

In order to confine the injected growth factor from freely diffusing, the growth factor can be embedded in a slow-release formula that gradually degrades or otherwise releases the growth factor over time in order to provide a sustained directional signal for the growth of the nerve cells. Such material can be porous polyspheres that may or may not be magnetic and which are large enough to be held in a fixed position by the solidified gel matrix of the Fibermag injected material.

The alignment of the magnetic particles or magnetic compound particles or fibers in the injected Fibermag plug is achieved by an externally applied magnetic field. For this application, it is not desirable that the particles are collected in any particular point, but the goal is to align the particles in the cavity of the spinal cord lesion without changing their overall homogeneous distribution and concentration as they were injected. In order to achieve this, it is preferable that a homogeneous magnetic field is applied where the magnetic field lines are aligned in the direction in which the nerve cells are intended to grow and connect.

Non-homogeneous magnetic fields (i.e. magnetic fields with a significant field gradient) will trigger a translational movement of the magnetic particles towards the higher field gradient. The amount of this movement is dependent on the magnetic moment of the magnetic particle, the strength of the magnetic field and the gradient, as well as on several other factors. It is possible to create magnetic fields from an external source that are near homogeneous therefore and do not exhibit any significant field gradient over the treatment area.

Such approximately homogeneous fields across the treatment area can easily be generated by external means without the need for internal magnetic coils or magnetic materials that are located inside the body. However this is an option for particular instances when the affected area is available for access, for instance during surgery. Two examples are the temporary placement/closure of conductive coils around the spine and the alignment of coils very close to the spine so that the magnetic field is created either inside the coils so that it directs the magnetic particle orientation, or that the field outside of the coils is sufficiently homogeneous to create parallel field lines without significant magnetic field gradient across the treatment area.

The latter is clearly advantageous because it is easier to administer and much less invasive. The fields outside of a field generating coil or sets of coils can be further controlled by differently shaped soft magnetic materials of various shapes which can be modeled in a way that the external magnetic field follows a more or less parallel direction in the desired orientation across the treatment area. It is not important that the field is homogenous in other parts of the body where there are no Fibermag magnetic materials injected. The solidification or polymerization or scaffolding of the Fibermag matrix can be achieved by a variety of means. There are many biocompatible materials available that are used to cure or form certain shapes in the body.

It is also possible to construct gel matrices with embedded cells or other components that aid in the regeneration of directional axonal growth. Layer by layer building of such matrix/cell structures can form defined tissue constructs. Embedding specific types of cells in aligned matrix scaffolds allows additional control of cell migration, interconnection and matrix remodeling in isotropic and anisotropic applications.

Invention Disclosure for Magnetically Alignable Electrospun Poly Lactide Fibers Supporting Documents Background Biomaterial approaches for spinal cord injury have shown that an aligned structure is an effective way to guide regenerating neurons and glia from the regenerating stumps of healthy tissue. The aligned structures are called conduits. Despite the many benefits of conduits, the primary drawback is that they are large rigid structures that must be delivered using invasive surgery. Furthermore, the regular geometry of conduits requires that the surgeon cut away healthy tissue to fit the biomaterial conduit into the injury site. The method to circumvent this invasive surgery is to prepare a biomaterial hydrogel that can be injected into the injury site and solidify in place. This uses non-invasive techniques and fills the irregular geometry of the lesion site, but lacks alignment. Aligned electrospun fibers are a promising application in guiding regeneration after spinal cord injury as a conduit.

We hypothesized that we could suspend electrospun fibers in an injectable hydrogel and align them using a magnetic field. A fiber/hydrogel composite would combine the benefits of an aligned conduit and an injectable hydrogel.

Purpose:

To develop a hydrogel-electrospun fiber composite that is capable of being injected into a spinal cord injury then aligned with an external magnetic field.

Methods:

The electrospun fibers are composed of a composite of high molecular weight poly-1-lactic acid (PLLA) and superparamagnetic iron oxide nanoparticles (SPION) that have a coating of oleic acid. The SPION particles are approximately 20 nm in diameter, and the oleic acid coating allows the particles to dissolve in an organic solvent. The fibers are aligned in a 1% agarose hydrogel.

Solution Preparation:

The solution is composed of PLLA, Chloroform, and SPION particles. The PLLA makes up 8% wt/wt of the chloroform. The final SPION particle concentration makes up 6% wt/wt of the PLLA. To prepare the solutions, 3 grams of chloroform are weighed into a 4 dram borosilicate glass vial and capped. 6% wt SPION/wt PLLA is weighed out on the balance and added to the chloroform solution. The SPION/Chloroform solution is mixed on a variable speed shake plate (250 rpm) until the nanoparticles have fully dissolved. Meanwhile 240 mg of PLLA (8% wt PLLA/wt chloroform) is weighed and added to the solution once the nanoparticles have dissolved. The solution is agitated for 3-4 hours on at 250 rpm on the variable speed shaker, or until the PLLA is dissolved. The solution is agitated in the absence of a magnetic field. After all components of the solution are fully dissolved, the solution is loaded into a 5 ml syringe for electrospinning.

Electrospinning Apparatus:

Electrospun fibers were prepared in a dissipative PVC glove box to control the humidity and reduce solvent exposure of the user. For the electrospinning device: a variable speed syringe pump holds a 5 mL syringe fitted with a 22 gauge needle. The syringe contains the electrospinning solution. A high voltage power source is connected to the needle that is located 5 cm above a grounded rotating collection disc (1 cm thick and 22 cm in diameter). The syringe pump extrudes the polymer solution at a consistent rate. As the polymer is exposed to the electric field it elongates into fibers and is spooled onto the collection disk. The electrospinning parameters used for this application are: Voltage 10.0 Kv, Pump rate 2.0 ml/hr, Collection time 10 min, Wheel Rotation Speed 500 rpm, and Humidity 22-32%.

Agarose Hydrogel Preparation:

500 μl a 1% wt agarose/volume phosphate buffered saline (PBS) was prepared in a 1.7 ml centrifuge tube and heated in a 100° C. heat block for 5 minutes. Twice during the heating the agarose solution was briefly vortexed to ensure the mixture was homogeneous. The fibers were cut to 1 cm, plasma treated for 90 sec to make the fibers hydrophilic, then immersed in the hydrogel solution. After alignment using the magnetic field shown below, the agarose was cooled to 4° C. for 10 minutes to form the hydrogel. We tested the hydrogel stiffness using a rheometer. The samples were incubated on the rheometer under a 20 mm diameter test geometry. The incubation step was followed by a time sweep using a 1% strain and 0.1 Hz frequency. The Incorporation of fibers did not significantly change the stiffness compared to an agarose hydrogel alone.

Fiber Optimization:

The 6% SPION concentration was determined through an optimization experiment in which 0.5%, 1%, 2%, 3%, 4%, 6%, and 8% wt SPION/wt PLLA solutions were electrospun. Of these, the 0.5% and 1% solutions yielded fibers that did not respond to the magnetic field. The 8% fibers could not fully form fibers given the above collection parameters. So initial testing was performed on the 2%, 4%, and 6% fibers. The fibers are shown below after being removed from the collection wheel. Increased SPION particle content can be related to a darker color of the fibers.

SEM images taken at each concentration of SPION fibers (2%=10 μm, 4%=50 μm. Fibers ranged from 2-3 μm in diameter and there was an increase in fiber diameter associated with increased SPION content. We established a magnetic field by placing two 2Tesla magnets in a 24 well plate. The fibers were placed horizontal to the field and images were taken as the fibers aligned. The 2% SPION fibers responded to the field by pulling toward one pole or the other, but the fibers did not have enough magnetic response to align. The 4% SPION fibers responded by aligning, but the process was slow compared to the 6% SPION fibers. Our apparatus was not capable of taking images at equal time intervals, so the images do not account for time. In fact the 6% SPION fibers aligned so fast that it was difficult to take a series of pictures.

We claim:

1. A method of regenerating a nerve fiber in a damaged neural tissue of a patient, the method comprising the steps of:
   administering an aqueous formulation of superparamagnetic particles and a biocompatible hydrogel matrix forming compound to the damaged neural tissue in the patient,
   applying a magnetic field in an orientation which is parallel to the nerve fiber;
   using the magnetic field for aligning the superparamagnetic particles;
   forming one or more aligned chains of the superparamagnetic particles in the magnetic field as a scaffold to guide directional growth of regenerating nerve cells; and
   reconnecting damaged nerve ends in the damaged neural tissue of the patient.

2. The method according to claim 1, further comprising an earlier step of functionalizing surfaces of the superparamagnetic particles with one or more chemical moieties prior to administering the aqueous formulation of the superparamagnetic particles and the biocompatible hydrogel matrix forming compound to the damaged neural tissue in the patient,
   wherein the surfaces of the superparamagnetic particles are functionalized with the one or more chemical moieties selected from the group consisting of:
   a carbohydrate, a protein, a lipid, a glass, an oligosaccharide, a peptide, a laminin, a biotin, an avidin, a streptavidin, a DNA, a cross-linking agent, a thiol, a sulfide, an oxide, a sulfhydryl, a sulfide, a disulfide, a sulfinyl, a sulfoxide, a sulfonyl, a sulfone, a sulfinic acid, a sulfino, a sulfonic acid, a sulfo, a thioketone, a carbonothioyl, a thial, a primary amine, a secondary amine, a tertiary amine, a carboxylate, a carboxyl, an alkoxy, a hydroperoxy, a peroxy, an alkyl, an alkene, an alkyne, an aryl derivative, a halo group, a hydroxyl, a carbonyl, an aldehyde, an acyl halide, an ester, a carbonate ester, an ether, a hemi-acetal, a hemiketal, a ketal, an orthoester, a methylenedioxy, a cycloalkyl, a heterocyclic, a heteroaryl, an orthocarbonate ester, a carboxamide, a primary ketimine, a secondary ketimine, a primary aldimine, a secondary aldimine, an imide, a nitro, a phosphonic acid, a phosphate, a phosphodiester, a nitrile, an isonitrile, an isocyanate, an antibody, a pharmaceutical excipient, a pH buffer, a cerium oxide nanoparticle, a manganese dioxide nanoparticle, EDTA, EGTA, NTA, HEDTA, a cytokine, and a combination thereof.

3. The method according to claim 2, wherein the earlier step of functionalizing the surfaces of the superparamagnetic particles with the one or more chemical moieties is for promoting a chemical bonding between the superparamagnetic particles when the magnetic field is aligning the superparamagnetic particles and forming the one or the more aligned chains of the superparamagnetic particles parallel to the nerve fiber.

4. The method according to claim 2, wherein the earlier step of functionalizing the surfaces of the superparamagnetic particles with the one or more chemical moieties is for forming Janus superparamagnetic particles.

5. The method according to claim 4, wherein the functionalized Janus superparamagnetic particles have a Side A surface functionalized with a first chemical moiety and have a Side B surface functionalized with a second chemical moiety.

6. The method according to claim 5, wherein the earlier step of functionalizing the surfaces of the superparamagnetic particles with the one or more chemical moieties for forming the Janus superparamagnetic particles is conducted in the presence of the magnetic field.

7. The method according to claim 5, wherein the functionalized Janus superparamagnetic particles have the Side A surface functionalized with the first chemical moiety as the thiol and have the Side B surface functionalized with the second chemical moiety as the primary amine.

8. The method according to claim 5, wherein the functionalized Janus superparamagnetic particles have the Side A surface functionalized with the first chemical moiety as the carboxylic acid and have the Side A surface functionalized with the second chemical moiety as the primary amine.

9. The method according to claim 1, wherein the aqueous formulation of the superparamagnetic particles and the biocompatible hydrogel matrix forming compound further comprises a molecule selected from the group consisting of: a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4-sulfation on astrocyte-derived chondroitin sulfate proteoglycan, an inhibitor of chondroitin sulfate proteoglycan phosphacan, an inhibitor of chondroitin sulfate proteoglycan neurocan, a chondroitinase-ABC, an inhibitor of chondroitin sulfate proteoglycan 4, an inhibitor of neuron-glial antigen 2, an antibody to chondroitin sulfate proteoglycan 4, an antibody against neuron-glial antigen 2, an inhibitor of glial cell expression of chondroitin sulfate proteoglycan 4, an inhibitor of glial cell expression of neuron-glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI-35, an antibody against myelination inhibitory factor NOGO, an anti-oxidants, cerium oxide nanoparticles, an amino acid, a phospholipid, a lipid, a vitamin, an anticoagulant, and a combination thereof.

10. The method according to claim 1, wherein the damaged neural tissue of the patient is in the brain of the patient.

11. The method according to claim 1, further comprising the step of stabilizing the one or more aligned chains of the superparamagnetic particles in the magnetic field using a cross-linking polymer architecture for locking the one or more aligned chains of the superparamagnetic particles into place after the step in claim 1 of using the magnetic field for aligning the superparamagnetic particles and forming the one or more aligned chains of the superparamagnetic particles in the magnetic field as the scaffold to guide directional growth of regenerating nerve cells.

12. The method according to claim 11, wherein the cross-linking polymer architecture for stabilizing the one or more aligned chains of the superparamagnetic particles is selected from the group consisting of: a cross-linking homopolymer of the superparamagnetic particles, a cross-linking junction controlled branched polymer of the superparamagnetic particles, and a combination thereof.

13. The method according to claim 11, wherein the cross-linking polymer architecture for stabilizing the one or the more aligned chains of the superparamagnetic particles is formed using molecules selected from the group consisting of: psoralen, methyl methacrylate, avidin, streptavidin, antibodies, antigens, ligands, biotin, laminin, fluorescein, DNA, DNA origami, DNA dendrimers, aptamers, protein-protein binding, protein-DNA binding, metal ion chelators, His-tags, polyethylene glycol-linkers, agarose, acrylamide, collagen, phase transfer catalysts, and any combination thereof.

14. The method according to claim 11, further comprising the step of removing the magnetic field which is parallel to the nerve fiber after the step of stabilizing the one or more aligned chains of the superparamagnetic particles using the cross-linking polymer architecture.

15. The method according to claim 1, wherein the superparamagnetic particles have dimensions selected from the group consisting of between about 0.5 microns to about 10 microns in diameter, between about 0.1 microns to about 5 microns in diameter, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination thereof.

16. The method according to claim 1, wherein the magnetic field has a strength between about 5 milli Tesla to about 500 milli Tesla.

17. The method according to claim 1, wherein the damaged neural tissue of the patient is in the spinal cord of the patient.

18. The method according to claim 1, wherein the damaged neural tissue of the patient is in the peripheral nervous system of the patient.

19. The method according to claim 11, wherein the cross-linking polymer architecture for stabilizing the one or more aligned chains of the superparamagnetic particles is formed using molecules selected from the group consisting of avidin, streptavidin, biotin, laminin, DNA, and any combination thereof.

20. The method according to claim 1, further comprising: an earlier step of placing a healthy section of neural tissue from the patient into an area of the damaged neural tissue of the patient prior to the step of administering the aqueous formulation of the superparamagnetic particles and the biocompatible hydrogel matrix forming compound to the damaged neural tissue in the patient.

* * * * *